United States Patent
Grant et al.

(10) Patent No.: US 8,133,666 B2
(45) Date of Patent: Mar. 13, 2012

(54) METHOD FOR IDENTIFYING AGENTS CAPABLE OF INHIBITING APOBEC3C ACTIVITY IN HIV-INFECTED CELLS

(75) Inventors: Robert M. Grant, San Francisco, CA (US); Khaoula Bourara, San Francisco, CA (US)

(73) Assignee: The J. David Gladstone Institutes, San Francisco, CA (US)

( * ) Notice: Subject to any disclaimer, the term of this patent is extended or adjusted under 35 U.S.C. 154(b) by 740 days.

(21) Appl. No.: 11/577,077

(22) PCT Filed: Oct. 31, 2005

(86) PCT No.: PCT/US2005/039522
§ 371 (c)(1),
(2), (4) Date: Dec. 11, 2008

(87) PCT Pub. No.: WO2006/065377
PCT Pub. Date: Jun. 22, 2006

(65) Prior Publication Data
US 2009/0105187 A1   Apr. 23, 2009

Related U.S. Application Data

(60) Provisional application No. 60/624,664, filed on Nov. 2, 2004.

(51) Int. Cl.
*C12Q 1/70* (2006.01)
*A61K 39/21* (2006.01)
(52) U.S. Cl. ......................... 435/5; 424/208.1
(58) Field of Classification Search ............... None
See application file for complete search history.

(56) References Cited

U.S. PATENT DOCUMENTS 7,220,554 B2 * 5/2007 Kabat et al. ............... 435/7.1

OTHER PUBLICATIONS

Yu, Q., 2004, APOBEC3B and APOBEC3C are potent inhibitors of simian immunodeficiency virus replication, J. Biol. Chem. 279(51):53379-53386 (published Oct. 4, 2004).*
Bourara, K., et al., 2007, Target cell APOBEC3C can induce limited G-to-A mutation in HIV-1, PLoS Pathogens, 3(10):1477-1485.*
Yu, Q., et al., 2004, APOBEC3B and APOBEC3C are potent inhibitors of simian immunodeficiency virus replication, J. Biol. Chem. 279(51):53379-53386.*
Blanc et al., Identification of GRY-RBP as an Apolipoprotein B, RNA-binding Protein That Interacts with Both Apobec-1 and Apobec-1 Complementation Factor to Modulate C to U Editing. The Journal of Biological Chemistry, 2001, vol. 276, No. 13, pp. 10272-10283.
Blanc et al., A Novel nuclear Localization Signal in the Auxiliary Domain of APOBEC-1 Complementing Factor Regulates Nucleocytoplasmic Import and Shuttling. The Journal of Biological Chemistry, 2003, vol. 278, No. 42, pp. 41198-41204.
Greeve et al., Inhibition of the Aprolipoprotein B mRNA Editing Enzyme-Complex by hmRNP V1 Protein and 40S hmRNP Complexes. Biological Chemistry 1998, vol. 379, pp. 1063-1073.
Harris et al., RNA editing Enzyme APOBEC1 and Some of its Homolgos Can Act as DNA Mutators. Molecular Cell, 2002, vol. 10, pp. 1247-1253.
Ragheb et al., Inhibition of Human Immunodeficiency Virus Type 1 by Tat/Rev-Regulated Expression of Cytosine Deaminase, Interferon alpha2, or Diphtheria Toxin Compared with Inhibition by Transdominant Rev. Human Gene Therapy, 1999, vol. 10, pp. 103-112.
Bourara et al., "Target Cell APOBEC3C Can Induce Limited G-to-A Mutation in HIV-1" *PLoS Pathogens*, 2007; 3(10):e153.

* cited by examiner

*Primary Examiner* — Jeffrey S. Parkin
(74) *Attorney, Agent, or Firm* — Paula A. Borden; Bozicevic, Field & Francis LLP.

(57) ABSTRACT

The present invention provides methods of identifying agents that reduce a level of active APOBEC3C in a cell. The present invention provides agents that reduce a level of active APOBEC3C in a cell; and compositions comprising the agents. The present invention further provides methods of reducing the mutation rate of a lentivirus in a cell; and methods of reducing the emergence of drug-resistant strains of lentivirus. The present invention further provides methods for treating lentivirus infections.

8 Claims, 10 Drawing Sheets

FIG. 2A

```
                         10         20         30         40
210W Plasmid  TCAGATCACTCTTTGGCAACGACCCCTCGTCACAATAAAG
210W in PBMC  ...A.................A.................
  210W in H9  ...A.................A................A
210W in CEMS S ...A...................................
 210W in 293T ...A...................................
 210W in Magi ...A...................................
210W in SupT1 ........................................
                         50         60         70         80
210W Plasmid  ATAGGGGGGCAACTAAAGGAAGCTCTATTAGACACAGGAG
210W in PBMC  ..............G.AA............A.....AA..
  210W in H9  ...A..............AA..........A.........
210W in CEMS S ..................A...........A.........
 210W in 293T ..................A...........A.........
 210W in Magi ..................A...................A..
210W in SupT1 ........................................
                         90        100        110        120
210W Plasmid  CAGATGATACAGTATTAGAAGAAATGAATTTGCCAGGAAG
210W in PBMC  ..A..A............A..A...A.........AA..A
  210W in H9  ..A..A............A..A...A.........AA..A
210W in CEMS S .....A.............A...A..............A
 210W in 293T ..A..A............A..A...A.............A
 210W in Magi .....A............A..A...A..........A..A
210W in SupT1 ........................................
                        130        140        150        160
210W Plasmid  ATGGAAACCAAAAATGATAGGGGAATTGGAGGTTTTATC
210W in PBMC  ..AA............A...AAAAA....AA.AA......
  210W in H9  ..AA............A...A...A....AA.........
210W in CEMS S ...A........................A..........
 210W in 293T ..AA............A...........AA..........
 210W in Magi ...A............A.....AAA....AA.A.......
210W in SupT1 ........................................
                        170        180        190        200
210W Plasmid  AAAGTAAGACAGTATGATCAGATACCAATAGAAATCTGCG
210W in PBMC  .......A......A....A...........A........A
  210W in H9  ......A.......A....A............A........
210W in CEMS S .........A...........A....................
 210W in 293T ..............A....A............A........
 210W in Magi .......A......A....A............A........
210W in SupT1 .........................................
```

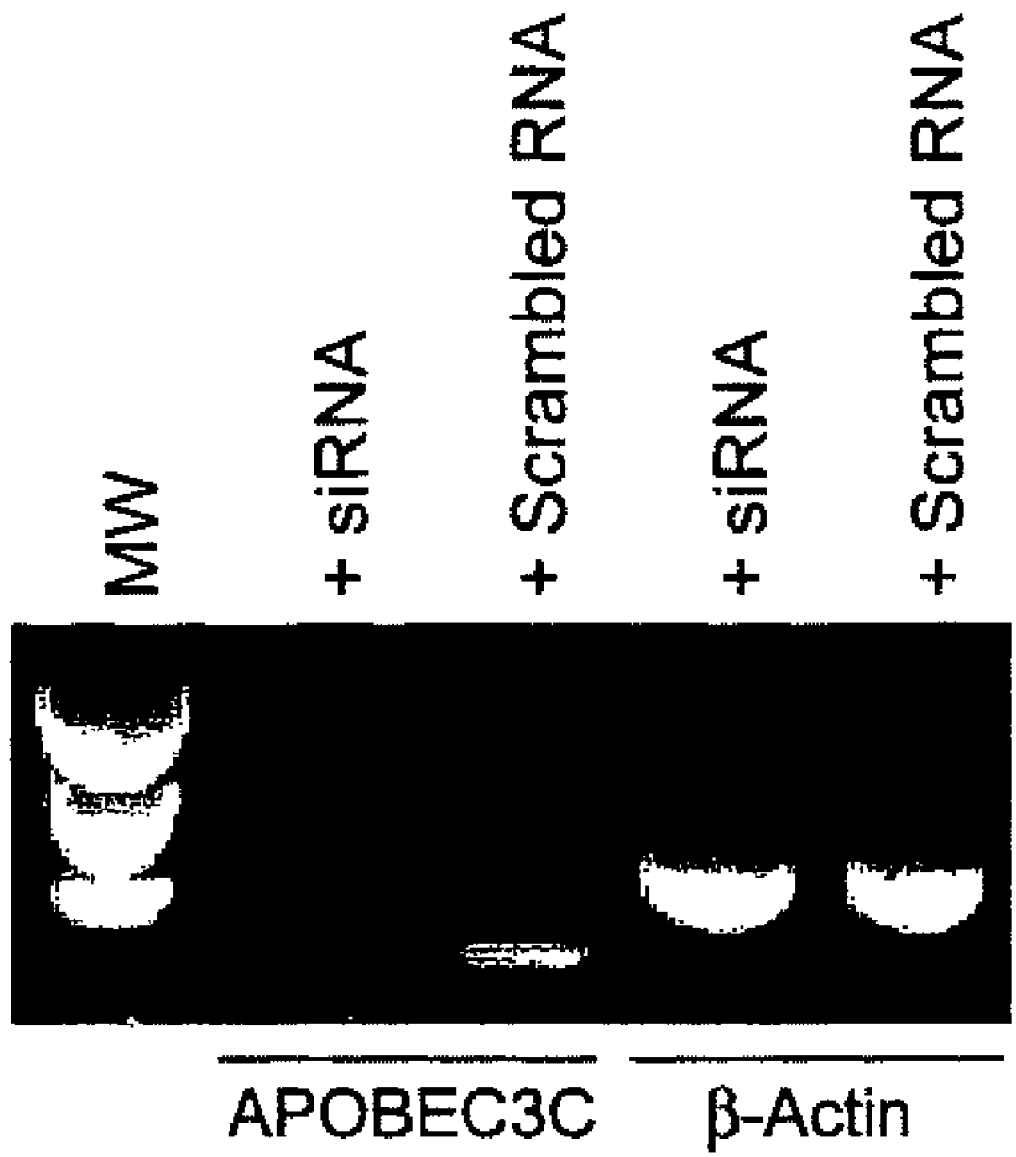

FIG. 4B

```
                              10         20         30         40
        210W Plasmid  TCAGATCACTCTTTGGCAAGACCCCTCGTCACAATAAAG
210W in Magi + Scrambled RNA  .........................A............
         210W in Magi + siRNA  ......................................

50         60         70         80
        210W Plasmid  ATAGGGGGCAACTAAAGGAAGCTCTATTAGACACAGGAG
210W in Magi + Scrambled RNA  .......................A.............A.
         210W in Magi + siRNA  ......................................

90        100        110        120
        210W Plasmid  CAGATGATACAGTATTAGAGAAATGAATTTGCCAGGAAG
210W in Magi + Scrambled RNA  ......A...........A..A........A....A..A
         210W in Magi + siRNA  ......................................

130        140        150        160
        210W Plasmid  ATGGAAACCAAAAATGATAGGGGGAATTGGAGGTTTTATC
210W in Magi + Scrambled RNA  ...A..........A.....AAA....AA..A........
         210W in Magi + siRNA  ........................................

170        180        190        200
        210W Plasmid  AAAGTAAGACAGTATGATCAGATACCAATAGAAATCTGCG
210W in Magi + Scrambled RNA  .......A.......A......A..............A.
         210W in Magi + siRNA  ........................................
```

FIG. 6

```
  1 mnpqirnpmk amypgtfyfq fknlweandr netwlcftve gikrrsvvsw ktgvfrnqvd
 61 sethchaerc flswfcddil spntkyqvtw ytswspcpdc agevaeflar hsnvnltift
121 arlyyfqypc yqeglrslsq egvaveimdy edfkycwenf vyndnepfkp wkglktnfrl
181 lkrrlreslq (SEQ ID NO:4)
```

METHOD FOR IDENTIFYING AGENTS CAPABLE OF INHIBITING APOBEC3C ACTIVITY IN HIV-INFECTED CELLS

CROSS-REFERENCE

This application claims the benefit of U.S. Provisional Patent Application No. 60/624,664, filed Nov. 2, 2004, which application is incorporated herein by reference in its entirety.

STATEMENT REGARDING FEDERALLY SPONSORED RESEARCH

The U.S. government has certain rights in this invention, pursuant to grant no. P01 HD40543 awarded by the National Institutes of Health.

FIELD OF THE INVENTION

This invention is in the field of lentivirus infections, particularly immunodeficiency virus infections.

BACKGROUND OF THE INVENTION

Human immunodeficiency virus (HIV) is the etiologic agent of acquired immunodeficiency syndrome (AIDS). HIV infection leads to depletion of CD4$^+$T lymphocytes. AIDS is characterized by various pathological conditions, including immune incompetence, opportunistic infections, neurological dysfunctions, and neoplastic growth.

The evolutionary success of primate lentiviruses is evident in their high prevalence in old-world primates, and their capacity to spread to new host species, frequently leading to the emergence of zoonotic disease. Their capacity to establish persistent infection in individual hosts also requires rapid and extensive viral adaptation which allows viral escape from humoral and cell-mediated immune responses. Viral adaptation to antiviral drugs underlies drug resistance which limits therapy for many patients. High rates of mutation contribute to high adaptive capacity of primate lentiviruses, and arise from the low fidelity of reverse transcriptase and RNA transcriptase II that are involved in replication of the viral genome. The mutagenic action of cytidine deaminases, such as APOBEC-3G, leads to hypermutation that is lethal. The role of this interaction in viral evolution is limited by its lethal phenotype, which restricts spread of possibly adaptive mutants, and the action of HIV-1 virion infectivity factor (Vif) which suppresses APOBEC-3G action by targeting the protein for ubiquitination.

One of the striking traits of HIV-1 genetic variation is G to A hypermutation, that is substitution of G residues for A in the proviral DNA as compared to the genomic RNA strand. G to A transition is strongly associated with the dinucleotide context decreasing in the order GA>GG>GT>GC. All parts of the retroviral genome can be susceptible to this process. Hypermutation occurs during reverse transcription when the minus DNA strand is synthesized.

Several recent reports have shown that a principal mechanism of G to A hypermutation is achieved by direct cytidine deamination of the retroviral minus stand cDNA during the reverse transcription. Cytidine residues are deaminated to uridine residues and this gives rise to G to A changes on the plus cDNA strand. Mutation within a GG context seems to be the consequence of APOBEC3G (h3$\overline{G}$) action. APOBEC3G inhibits the replication of wide range retroviruses by mediating the lethal deamination of Cs to Us as the retroviral RNA is copied into DNA. APOBEC3G belongs to a family of ten cytidine deaminase genes that in humans includes APOBEC1, APOBEC2, AID and APOBEC3A to 3G. APOBEC3F (h3F) and APOBEC3B (h3B) create lethal G to A changes in the newly synthesized virus. These mutations may result in a virus that is degraded or nonfunctional. Anti-retroviral activity of h3G, h3F, and h3B requires their encapsidation into assembling virions. However, HIV-1 encodes a protein Vif (virion infectivity factor) that reduces their incorporation into virions, possibly by promoting their degradation via the ubiquitin-proteasome pathway. A single amino acid change at residue 128 in the N terminal region of APOBEC30 determines the specificity for Vif susceptibility. The protein domain coded by residues 104-156 in the N terminal region of h3G is required for its incorporation into the virus.

Hypermutants have been identified in a single cycle of reverse transcription with wild type viruses. In clinical isolates, hypermutation occurs preferentially within a GA context. h3F and h3B have a GA context preference but the activity of h3F is susceptible to HIV-1 Vif and the expression of h3B is absent in PBMC susceptible to HIV-1 infection. Detection of HIV-1 hypermutated sequences in at least 43% of patients suggests that hypermutation may happen in a systematic way in HIV-1-infected individuals and may be associated with a viral mechanism to prevail in a hostile environment.

Several drugs, have been approved for treatment of AIDS, including azidovudine (AZT), didanosine (dideoxyinosine, ddI), d4T, zalcitabine (dideoxycytosine, ddC), nevirapine, lamivudine (epivir, 3TC), abacavir (Ziagen), tenofovir (Viread, TDF), emtricitabine (Emtriva, FTC), saquinavir (Invirase or Fortovase), ritonavir (Norvir), nelfinavir (Viracept), indinavir (Crixivan), amprenavir (Agenerase), fosamprenavir (Lexiva), atazanavir (Reyataz), efavirenz (Sustiva), lopinavir/ritonavir (Kaletra), delavirdine (Rescriptor), and enfurvitide (Fuzeon, T-20). However, none of the available drugs used to combat HIV is completely effective, and treatment frequently gives rise to drug-resistant virus.

Despite the availability of a number of drugs to combat HIV infections, there is a need in the art for additional drugs that inhibit HIV replication, as well as drugs that inhibit viral mutation and the resulting emergence of variant strains that evade host immune response(s) and/or that are resistant to anti-retroviral drugs, which drugs are suitable for treating HIV and other lentiviral infections. The present invention addresses this need by providing methods for identifying agents that inhibit APOBEC3C activity; and by providing therapeutic regimens for treating HIV and other lentivirus infections.

Literature

Harris et al. (2002) *Mol. Cell.* 10:1247-1253; Yu et al. (Oct. 8, 2004) *J. Biol. Chem.* Manuscript M408802200; U.S. Patent Publication No. 20040175743; Fitzgibbon et al. (1993) *AIDS Res Hum Retroviruses* 9:833-838; and Vartanian et al. (1991) *J Virol* 65:1779-1788.

SUMMARY OF THE INVENTION

The present invention provides methods of identifying agents that reduce a level of active APOBEC3C in a cell. The present invention provides agents that reduce a level of active APOBEC3C in a cell; and compositions comprising the agents. The present invention further provides methods of reducing the mutation rate of a lentivirus in a cell; and methods of reducing the emergence of drug-resistant strains of lentivirus. The present invention further provides methods for treating lentivirus infections.

BRIEF DESCRIPTION OF THE DRAWINGS

FIGS. 2A-C depict G-to-A mutations in various cells. FIG. 2A depicts viral DNA sequences from cells 5 days after infection (210W plasmid: SEQ ID NO5; 210W in PBMC: SEQ ID NO:6; 210W in H9: SEQ ID NO:7; 210W in CEMS S: SEQ ID NO:8; 210W in 293T: SEQ ID NO:9; 210W in Magi: SEQ ID NO:10; 210W in SupT1: SEQ ID NO:5). FIG. 2B depicts the G-to-A hypermutation profile in PMBC and CEMSS. FIG. 2C depicts the G-to-A hypermutation profiled in 293T cells and Magi cells.

FIGS. 4A and 4B depict inhibition of APOBEC3C expression by siRNA (FIG. 4A); and G to A hypermutation (FIG. 4B). 210W plasmid: SEQ ID NO:5; 210W in Magi+scrambled RNA: SEQ ID NO:11; 210W in Magi+siRNA: SEQ ID NO:5).

FIG. 5A depicts APOBEC3C protein expression in 293T cells. FIG. 5B depicts the efficiency of transfection of SupT1 cells. FIG. 5C depicts the distribution of G to A mutations in viral DNA.

FIG. 6 provides the amino acid sequence of a human APOBEC3C enzyme (SEQ ID NO:4).

DEFINITIONS

Figure 1:
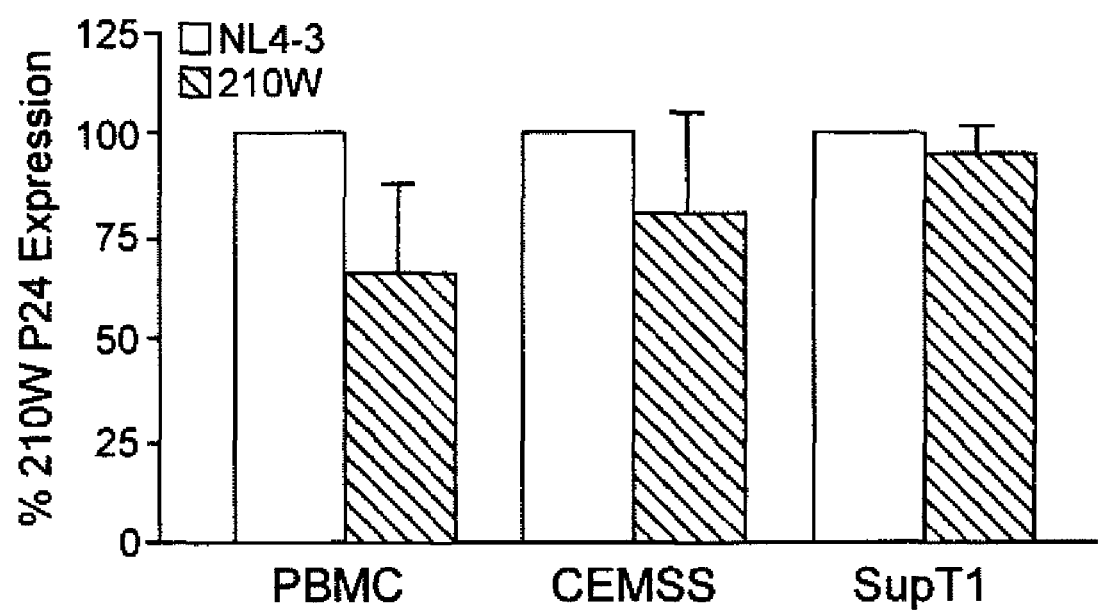
FIG. 1 depicts replication of NL4-3 and 210W in three cell types.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease. In the context of lentivirus infection, the term "treatment" encompasses prevention of establishment of a systemic infection following initial contact with the virus; and prophylactic treatment of an individual not yet infected with the virus.

The terms "individual host," "subject," and "patient," used interchangeably herein, refer to a mammal, including, but not limited to, murines, felines, simians, humans, mammalian farm animals, mammalian sport animals, and mammalian pets. The term includes mammals that are susceptible to infection by a lentivirus. In many embodiments, treatment of humans is of interest.

The terms "$CD4^+$-deficient" and "$CD4^+$-low" are used interchangeably herein, and, as used herein, refer to a state of an individual in whom the number of $CD4^+$T lymphocytes is reduced compared to an individual with a healthy, intact immune system. $CD4^+$ deficiency includes a state in which the number of functional $CD4^+$T lymphocytes is less than about 600 $CD4^+$T cells/$mm^3$ blood; a state in which the number of functional $CD4^+$T cells is reduced compared to a healthy, normal state for a given individual; and a state in which functional $CD4^+$T cells are completely absent.

As used herein, a "$CD4^+$-deficient individual" is one who has a reduced number of functional $CD4^+$-T cells, when compared to an individual having a normal, intact immune system. In general, the number of functional $CD4^+$-T cells that is within a normal range is known for various mammalian species. In human blood, e.g., the number of functional $CD4^+$-T cells which is considered to be in a normal range is from about 420 to about 1500 $CD4^+$-T cells/$mm^3$ blood. An individual having a number of $CD4^+$-T cells below the normal range, e.g., below about 420/$mm^3$, may be considered "$CD4^+$-deficient." Thus, a $CD4^+$-deficient individual may have a low $CD4^+$T cell count, or even no detectable $CD4^+$T cells.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as $CD4^+$T lymphocytes, glial cells, macrophages, tumor cells, peripheral blood mononuclear cells (PBMC), and the like. The term "biological sample" encompasses a clinical sample, and also includes cells in culture, cell supernatants, tissue samples, organs, bone marrow, and the like.

The term "lentivirus" as used herein, refers to human immunodeficiency virus-1 (HIV-1); human immunodeficiency virus-2 (HIV-2); simian immunodeficiency virus (SIV); and feline immunodeficiency virus (FIV).

As used herein, the term "endogenous nucleic acid" refers to a nucleic acid that is normally present in a given cell in nature and/or under normal in vitro culture conditions, e.g., the nucleic acid is normally present in the genome of the cell. As used herein the term "endogenous protein" refers to a protein that is normally synthesized by a given cell in nature and/or under normal in vitro culture conditions. In general, an endogenous protein is encoded by a nucleotide sequence present in an endogenous nucleic acid. As used herein, an "exogenous nucleic acid" refers to a nucleic acid that is not normally found in a given cell in nature and/or under normal in vitro culture conditions. An exogenous nucleic acid is generally introduced into the cell. As used herein, the term "exogenous protein" refers to a protein that is not normally produced by a given cell in nature and/or under normal in vitro culture conditions. In general, an exogenous protein is encoded by a nucleotide sequence present in an exogenous nucleic acid.

The term "transformation" is used interchangeably herein with "genetic modification" and refers to a permanent or transient genetic change induced in a cell following introduction of new nucleic acid (i.e., DNA exogenous to the cell). Genetic change ("modification") can be accomplished either by incorporation of the new DNA into the genome of the host cell, or by transient or stable maintenance of the new DNA as an episomal element. A permanent genetic change may be achieved by introduction of the DNA into the genome of the cell.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector that comprises a nucleotide sequence encoding one or more biosynthetic pathway gene products), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a nucleic acid, e.g., an expression vector, that comprises a nucleotide sequence encoding one or more biosynthetic pathway gene products. Similarly, a subject prokaryotic host cell is a genetically modified prokaryotic host cell (e.g., a bacterium), by virtue of introduction into a suitable prokaryotic host cell an exogenous nucleic acid, e.g., a nucleic acid that is foreign to the prokaryotic host cell; and a subject eukaryotic host cell is a genetically modified eukaryotic host cell, by virtue of introduction into a suitable eukaryotic host cell an exogenous nucleic acid, e.g., a nucleic acid that is foreign to the eukaryotic host cell.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "an APOBEC3C polypeptide" includes a plurality of such polypeptides and reference to "the APOBEC3C inhibitor" includes reference to one or more APOBEC3C inhibitors and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides methods of identifying agents that reduce a level of active APOBEC3C in a cell. The present invention provides agents that reduce a level of active APOBEC3C in a cell; and compositions comprising the agents. The present invention further provides methods of reducing the mutation rate of a lentivirus in a cell; and methods of reducing the emergence of drug-resistant strains of lentivirus. The present invention further provides methods for treating lentivirus infections.

Screening Methods

The present invention provides methods of identifying an agent that reduces the level of active APOBEC3C in a cell. The methods generally involve contacting an APOBEC3C protein with a test agent; and determining the effect, if any, of the test agent on the level of active APOBEC3C. A test agent that reduces the level of active APOBEC3C is a candidate agent for treating lentiviral infections.

As used herein, the term "active APOBEC3C" refers to a form of APOBEC3C that is enzymatically active and induces one or more mutations in a lentivirus genome. APOBEC3C proteins are known in the art, and the amino acid sequences of APOBEC3C protein from humans is known. For example, the amino acid sequence of human APOBEC3C is found under GenBank Accession Nos. Q9NRW3, NP_055323, and AAH11739. Nucleotide sequences encoding APOBEC3C are also known. For example, nucleotide sequences encoding APOBEC3C are found under GenBank Accession Nos. BC011739 and NM_014508.

The subject screening methods are carried out in vitro. In some embodiments, the methods are cell-based methods. In these embodiments, the methods generally involve contacting a cell with a test agent; and determining the effect, if any, of the test agent on the level of active APOBEC3C protein in the cell. In other embodiments, the methods are cell-free methods. A test agent of interest decreases the level of active APOBEC3C in a cell, regardless of the mechanism by which the decrease is achieved.

A subject assay for identifying agents that decrease the level of active APOBEC3C protein in a cell can be designed in a number of ways. In some embodiments, a subject assay for identifying an agent that decreases the level of active APOBEC3C involves determining the effect of a test agent on the level of APOBEC3C protein that induces a C→U mutation in minus strand DNA, resulting in a G→A mutation in viral plus strand DNA.

The terms "candidate agent," "agent," "substance," "test agent," and "compound" are used interchangeably herein. Candidate agents encompass numerous chemical classes, and are generally synthetic, semi-synthetic, or naturally-occurring inorganic or organic molecules.

In some embodiments, a candidate agent is a small organic compound having a molecular weight of more than 50 daltons and less than about 2,500 daltons.

Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

In other embodiments, a candidate agent has a molecular weight of greater than 2,500 daltons. In these embodiments, a candidate agent may be a peptide, an oligopeptide, a polypeptide, a carbohydrate, a polysaccharide, a lipid, a lipopolysaccharide, a glycoprotein, a proteoglycan, a lipoprotein, or other macromolecule.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

A candidate agent is assessed for any cytotoxic activity it may exhibit toward the cell used in the assay, using well-known assays, such as trypan blue dye exclusion, an MTT ([3-(4,5-dimethylthiazol-2-yl)-2,5-diphenyl-2H-tetrazolium bromide]) assay, and the like. Agents that do not exhibit significant cytotoxic activity are considered candidate agents.

Assays of the invention usually include one or more controls. Thus, a test sample includes a test agent, and a control sample has all the components of the test sample except for the test agent. Generally a plurality of assay mixtures is run in parallel with different agent concentrations to obtain a differential response to the various concentrations. Typically, one of these concentrations serves as a negative control, i.e. at zero concentration or below the level of detection.

A variety of reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as nuclease inhibitors, anti-microbial agents, etc. may be used. The components may be added in any order. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

It should be understood that a subject method that involves determining the effect of a test agent on the number of APOBEC3C-induced mutations in a lentivirus genome need not be carried out using the entire lentivirus genome. Instead, a portion of a lentivirus genome can be used to determine the effect of a test agent on the number of APOBEC3C-induced mutations in a lentivirus genome. Thus, the term "lentivirus nucleic acid," as used herein, thus includes all or a portion of a lentivirus genome, where the nucleic acid may be single stranded or double stranded. The term "lentivirus nucleic acid" includes nucleic acids that comprise, in addition to a lentivirus nucleotide sequence, a heterologous nucleotide sequence (e.g., non-lentivirus nucleotide sequences, such as nucleotide sequences encoding detectable markers; non-lentivirus control elements; and the like). The term "lentivirus nucleic acid" includes nucleic acids that comprise naturally-occurring lentivirus nucleotide sequences; variants of lentivirus nucleotide sequences; and synthetic lentivirus nucleotide sequences. The term "lentivirus nucleic acid" includes a nucleic acid that comprises lentivirus minus strand DNA. In many embodiments, for assays involving determining the number of mutations in a lentivirus genome, and in particular determining the number of APOBEC3C-induced mutation in a lentivirus genome, a lentivirus nucleic acid that includes lentivirus minus strand DNA is used.

Reducing a level of active APOBEC3C in a cell is accomplished by: a) reducing the level of APOBEC3C mRNA in a cell; and/or b) reducing the level of APOBEC3C protein in a cell; and/or c) reducing APOBEC3C enzymatic activity. In some embodiments, a test agent of interest is one that reduces a level of active APOBEC3C in a cell by at least about 10%, at least about 20%, at least about 25%, at least about 30%; at least about 35%, at least about 40%, at least about 45%, at least about 50%, at least about 55%, at least about 60%, at least about 65%, at least about 70%, at least about 80%, at least about 90%, or more, when compared to the level of active APOBEC3C in a control in the absence of the test agent.

In other embodiments, a test agent of interest is one that decreases the number of mutations (e.g., APOBEC3C-induced mutations) in a lentivirus nucleic acid by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or at least about 95%, or more, when compared to the number of mutations in the lentivirus nucleic acid in the absence of the test agent.

In many embodiments, a subject assay involves contacting a cell with a test agent, where the cell is one that synthesizes APOBEC3C mRNA and/or protein. In some embodiments, the cell is one that normally synthesizes APOBEC3C mRNA and/or APOBEC3C protein, e.g., the cell synthesizes APOBEC3C mRNA and/or protein encoded by an endogenous APOBEC3C gene. In other embodiments, the cell is one that does not normally synthesize APOBEC3C mRNA and/or protein; instead, the cell synthesizes APOBEC3C mRNA and/or protein that is encoded by an exogenous nucleic acid. In these embodiments, the cell is genetically modified with an exogenous nucleic acid that includes a nucleotide sequence that encodes an APOBEC3C protein.

Cell-based assays generally comprise the steps of contacting the cell with an agent to be tested, forming a test sample, and, after a suitable time, assessing the effect of the agent on APOBEC3C mRNA levels and/or APOBEC3C protein levels and/or APOBEC3C enzymatic activity levels. A control sample comprises the same cell without the candidate agent added. APOBEC3C mRNA levels and/or APOBEC3C protein levels and/or APOBEC3C enzymatic activity levels are measured in both the test sample and the control sample. A comparison is made between APOBEC3C mRNA levels and/or APOBEC3C protein levels and/or APOBEC3C enzymatic activity levels in the test sample and the control sample. APOBEC3C mRNA levels and/or APOBEC3C protein levels and/or APOBEC3C enzymatic activity levels can be assessed using conventional assays. For example, when a mammalian cell line is transformed with a construct that results in expression of APOBEC3C, APOBEC3C mRNA levels can be detected and measured, or APOBEC3C polypeptide levels can be detected and measured, or APOBEC3C enzymatic activity levels can be detected and measured. A suitable period of time for contacting the agent with the cell can be determined empirically, and is generally a time sufficient to allow entry of the agent into the cell and to allow the agent to have a measurable effect on APOBEC3C mRNA levels and/or APOBEC3C protein levels and/or APOBEC3C enzymatic activity levels. Generally, a suitable time is between 10 minutes and 24 hours, or from about 1 hour to about 8 hours.

Methods of Identifying an Agent that Reduces a Level of APOBEC3C Protein in a Cell In some embodiments, a subject screening method involves identifying an agent that reduces a level of APOBEC3C protein in a cell, by determining the effect of a test agent on the level of APOBEC3C protein in the cell. Thus, in some embodiments, the method involves contacting a cell with a test agent; and determining the effect, if any, of the test agent on the level of APOBEC3C protein in the cell.

In these embodiments, a test agent of interest reduces the level of APOBEC3C protein in a cell by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, compared the level of APOBEC3C protein in the cell in the absence of the test agent.

The APOBEC3C protein that is produced by the cell may have the amino acid sequence that is provided under one of GenBank Accession Nos. Q9NRW3, NP_055323, and AAH11739, or fragments or variants thereof. The APOBEC3C protein that is used can vary from the sequence provided under GenBank Accession Nos. Q9NRW3, NP_055323, and AAH11739 by from one to about 20 amino acids, e.g., the sequence can include from one to about 20 amino acid substitutions. The APOBEC3C protein may also be an enzymatically active fragment of a known APOBEC3C protein. Typically, the APOBEC3C protein that is used retains cytidine deaminase activity of the native, naturally-occurring protein. Suitable APOBEC3C proteins also include fusion proteins that include APOBEC3C and a heterologous protein (a "fusion partner") fused in-frame to the amino terminus or carboxyl terminus of the APOBEC3C protein. Suitable fusion partners include peptides and polypeptides that provide ease of purification, e.g., $(His)_n$, e.g., 6His, and the like; provide an epitope tag, e.g., glutathione-S-transferase (GST), hemagglutinin (HA; e.g., CYPYDVPDYA; SEQ ID NO; 1), FLAG (e.g., DYKDDDDK; SEQ ID NO:2), c-myc (e.g., CEQKLISEEDL; SEQ ID NO:3), and the like; peptides and polypeptides provide a detectable signal, e.g., an enzyme that generates a detectable product (e.g., β-galactosidase, luciferase, horse radish peroxidase, alkaline phosphatase, etc.), or a protein that is itself detectable, e.g., a fluorescent protein (e.g., a green fluorescent protein), etc.; and the like. In some embodiments, an APOBEC3C protein comprises the amino acid sequence set forth in SEQ ID NO:4, and shown in FIG. 6. In some embodiments, an APOBEC3C protein comprises a fragment of the amino acid sequence set forth in FIG. 6, where the fragment retains substantially all of the enzymatic activity of the full-length protein.

In many embodiments, the effect of a test agent on APOBEC3C protein levels in a cell is determined by introducing an expression vector, which includes an APOBEC3C coding sequence, into suitable eukaryotic cells in in vitro culture, generating genetically modified cells that produce APOBEC3C protein; contacting the genetically modified cells with a test agent; and determining the effect, if any, of the test agent on the level of APOBEC3C protein produced by the genetically modified cell.

Expression vectors that are suitable for expression in eukaryotic cells are constructed to include a coding region for an APOBEC3C protein (for production of APOBEC3C protein in the cell). An expression vector comprising an APOBEC3C coding region will generally include regulatory sequences ("control sequences" or "control regions") which are necessary to effect the expression of an APOBEC3C-coding polynucleotide to which they are operably linked. Expression vectors typically comprise a transcription initiation region, a promoter region, an APOBEC3C-coding nucleotide sequence, and a transcriptional termination region. Suitable promoters include constitutive promoters and inducible promoters, a number of which are well known in the art. Expression vectors generally have convenient restriction sites located near the promoter sequence to provide for the insertion of nucleic acid sequences encoding an APOBEC3C protein. A selectable marker operative in the expression host may be present.

Expression vectors are introduced into eukaryotic cells using any convenient means, including calcium phosphate precipitation; electroporation; infection (where the expression vectors are packaged into viral particles); liposome-mediated transfection; and the like. Suitable cells are eukaryotic cells, typically mammalian cells, including primary cells, immortalized cell lines, etc., including, but not limited to, COS cells, 293T cells, Jurkat cells, H9 cells, and the like.

Whether a test agent reduces the level of an APOBEC3C protein in a cell is readily determined using any of a variety of assays for detecting the presence and/or level of a protein in a cell. In some embodiments, the assay is an immunological assay, using a APOBEC3C-specific antibody. Such methods include, but are not limited to, immunoprecipitating APOBEC3C from a cellular extract, and analyzing the immunoprecipitated APOBEC3C by sodium dodecyl sulfate polyacrylamide gel electrophoresis (SDS-PAGE); detecting a detectable fusion partner in a cell that produces a fusion protein that includes APOBEC3C and a fusion partner that provides a detectable signal; standard SDS-PAGE and immunoblotting (e.g., transfer of proteins from a gel generated during SDS-PAGE to a membrane, and probing the membrane with detectably labeled antibodies) of APOBEC3C from cells producing APOBEC3C; and the like.

In other embodiments, the assay is an assay that detects a fusion partner of a APOBEC3C fusion protein. Thus, e.g., where the APOBEC3C is part of a fusion protein that includes APOBEC3C, and, as a fusion partner, a protein that provides a detectable signal, the assay detects the fusion partner. Fusion partners include, but are not limited to, a green fluorescent protein (GFP); a fluorescent protein from an *Anthozoa* species (see, e.g., Matz et al. (1999) *Nat. Biotechnol* 17:969-973); luciferase; β-galactosidase; horse radish peroxidase; alkaline phosphatase; and the like. A construct that includes a nucleotide sequence that encodes the APOBEC3C fusion protein is introduced into a eukaryotic cell. The level of APOBEC3C protein that is produced in the cell is determined by detecting the fusion partner. Immunological assays (protein blots, ELISAs, etc.) are used where the fusion partner is an immunological tag. Enzymatic assays are used where the fusion partner is an enzyme (e.g., β-galactosidase, luciferase, horse radish peroxidase, etc.) that produces a detectable product. Fluorimetric assays are used to detect fusion partners that are fluorogenic. A luminometer is used to detect fusion partners that yield a luminescent product. The fusion partner is detected by any known method appropriate to the fusion partner. The fusion partner is detected in a cell extract, using an assay appropriate to the fusion partner (e.g., an enzymatic assay, an immunological assay, etc.); or the fusion partner is detected in an intact cell, e.g., using flow cytometry. For example, where the fusion partner provides a fluorescent signal, the level of APOBEC3C is in some embodiments determined using a flow cytometer.

The following is one non-limiting example of a suitable assay for identifying agents that reduce a level of APOBEC3C protein in a cell. Mammalian cells (e.g., an immortalized cell line) are stably transfected with an expression vector that includes a coding sequence for a luciferase-APOBEC3C fusion protein, such that the cells synthesize the luciferase-APOBEC3C (luc-APOBEC3C) fusion protein. A substrate for luciferase is provided in the cell medium, such that the substrate enters the cell, and is acted on by the luciferase portion of the luciferase-APOBEC3C to yield a luminescent product. The level of luciferase in the cell is detected using a luminometer, and the level of luc-APOBEC3C is expressed as relative light units. The cells are contacted with a test agent. A test agent that reduces the level of the luc-APOBEC3C fusion protein reduces the relative light units in the cell, compared with the relative light units in a control cell that synthesizes luc-APOBEC3C, where the control cell is not contacted with the test agent.

An agent that reduces the level of APOBEC3C-luciferase protein in the cell by at least about 5%, at least about 10%, at least about 20%, at least about 30%, at least about 50%, at least about 75%, or at least about 95%, or more, is a candidate agent for treating a lentivirus infection.

Methods of Identifying Agents that Reduces a Level of APOBEC3C mRNA in a Cell

In some embodiments, a subject screening method involves determining the effect of a test agent on the level of APOBEC3C mRNA in a cell. Thus, in some embodiments, the method involves contacting a cell with a test agent; and determining the effect, if any, of the test agent on the level of APOBEC3C mRNA in the cell.

In these embodiments, a test agent of interest reduces the level of APOBEC3C mRNA in a cell by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, compared the level of APOBEC3C mRNA in the cell in the absence of the test agent.

Nucleotide sequences encoding APOBEC3C are also known. For example, nucleotide sequences encoding APOBEC3C are found under GenBank Accession Nos. BC011739 and NM_014508. In some embodiments, the APOBEC3C mRNA being detected is encoded by an exogenous nucleic acid. In many of these embodiments, the cell is one that does not synthesize endogenous APOBEC3C mRNA. In some embodiments, an exogenous nucleic acid comprising a nucleotide sequence encoding APOBEC3C is introduced into a cell, forming a genetically modified host cell that synthesizes exogenous APOBEC3C mRNA. In some of these embodiments, the nucleotide sequence encoding APOBEC3C differs from the nucleotide sequence disclosed in one of GenBank Accession Nos. BC011739 and NM_014508 by from about 1 nucleotide to about 50 nucleotides (or more.

In other embodiments, the exogenous nucleic acid comprises an APOBEC3C promoter operably linked to a reporter gene, e.g., a nucleotide sequence that encodes a detectable protein, e.g., a reporter protein such as a fluorescent protein (e.g., a green fluorescent protein); or an enzyme that yields a detectable protein, e.g., β-galactosidase, luciferase, horse radish peroxidase, alkaline phosphatase, etc. In these embodiments, the reporter gene product is detected, using methods that are standard in the art.

Methods of measuring APOBEC3C mRNA levels are known in the art, any known methods can be used in the methods of the present invention to identify an agent which reduces APOBEC3C mRNA level in a cell, including, but not limited to, a polymerase chain reaction (PCR), such as a PCR employing detectably labeled oligonucleotide primers, and any of a variety of hybridization assays.

A number of methods are available for analyzing nucleic acids for the presence and/or level of a specific mRNA in a cell. The mRNA may be assayed directly or reverse transcribed into cDNA for analysis. The nucleic acid may be amplified by conventional techniques, such as a PCR, to provide sufficient amounts for analysis. The use of the polymerase chain reaction is described in Saiki, et al. (1985), *Science* 239:487, and a review of techniques may be found in Sambrook, et al. *Molecular Cloning: A Laboratory Manual*, CSH Press 1989, pp. 14.2-14.33.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2′,7′-dimethoxy-4′,5′-dichloro-6-carboxyfluorescein (JOE), 6-carboxy-X-rhodamine (ROX), 6-carboxy-2′,4′,7′,4,7-hexachlorofluorescein (HEX), 5-carboxyfluorescein (5-FAM) or N,N,N′,N′-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

A variety of different methods for determining the nucleic acid abundance in a sample are known to those of skill in the art, where particular methods of interest include those described in: Pietu et al., Genome Res. (June 1996) 6: 492-503; Zhao et al., Gene (Apr. 24, 1995) 156: 207-213; Soares, Curr. Opin. Biotechnol. (October 1997) 8: 542-546; Raval, J. Pharmacol Toxicol Methods (November 1994) 32: 125-127; Chalifour et al., Anal. Biochem (Feb. 1, 1994) 216: 299-304; Stolz & Tuan, Mol. Biotechnol. (December 19960 6: 225-230; Hong et al., Bioscience Reports (1982) 2: 907; and McGraw, Anal. Biochem. (1984) 143: 298. Also of interest are the methods disclosed in WO 97/27317.

Methods of Identifying Agents that Reduce a Level of Active APOBEC3C in a Cell

In some embodiments, the invention provides methods of identifying an agent that reduces a level of active APOBEC3C in a cell. In these embodiments, a subject screening method involves determining the effect of a test agent on the level of active APOBEC3C protein in a cell. The method generally involves contacting a cell that produces APOBEC3C with a test agent; and determining the effect, if any, of the test agent on the level of active APOBEC3C protein in the cell.

In these embodiments, a test agent of interest is one that reduces the level of active APOBEC3C in a cell by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, when compared to the level of active APOBEC3C in a control cell in the absence of the test agent.

In other embodiments, a test agent of interest is one that reduces the number of mutations (e.g., APOBEC3C-induced mutations) in a lentivirus nucleic acid by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, or at least about 90%, or more, when compared to the number of mutations in the lentivirus nucleic acid in the absence of the test agent.

In some embodiments, a test agent of interest is one that reduces the number of C→U mutations in a minus strand of a lentivirus by at least about 5%, at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, or at least about 90%, or more, when compared to the number of C→U mutations in a minus stand of a lentivirus in the absence of the test agent.

In some embodiments, the cell is one that produces endogenous APOBEC3C. In other embodiments, the effect of a test agent on the level of active APOBEC3C protein in a cell is determined by introducing an expression vector, which includes an APOBEC3C coding sequence, into suitable eukaryotic cells in in vitro culture, generating genetically modified cells that produce APOBEC3C protein; contacting the genetically modified cells with a test agent; and determining the effect, if any, of the test agent on the level of active APOBEC3C protein produced by the genetically modified cell.

The level of active APOBEC3C in a cell can be determined in various ways. In some embodiments, a subject assay for identifying an agent that reduces production of active APOBEC3C in a cell involves determining the effect of the agent on the level of APOBEC3C production. In some embodiments, a subject assay for identifying an agent that reduces the level of active APOBEC3C involves determining the effect of a test agent on the level of APOBEC3C protein that induces a C→U mutation in a minus strand, resulting in a G→A mutation in viral reverse transcripts and/or that induces a C→T mutation in a DNA copy.

Where a subject assay for identifying an agent that reduces the level of active APOBEC3C in a cell involves determining the effect of a test agent on the level of synthesis of APOBEC3C by the cell, the assay can be conducted in a number of ways. For example, synthesis of APOBEC3C by the cell can be detected using a cell that produces APOBEC3C; contacting the cell with a test agent; and detecting the level of APOBEC3C protein using an immunoblot assay with antibody specific for APOBEC3C, or an ELISA assay with antibody specific for APOBEC3C. The cells are typically lysed to release the APOBEC3C. As another example, synthesis of APOBEC3C by the cell can be detected using a cell that includes an expression construct that comprises a nucleotide sequence that encodes APOBEC3C under control of an APOBEC3C promoter; contacting the cell with the test agent; and detecting the level of APOBEC3C protein using an immunoblot assay with antibody specific for APOBEC3C, or an ELISA assay with antibody specific for APOBEC3C. As another non-limiting example, synthesis of APOBEC3C by the cell can be detected using a cell that includes an expression construct that comprises a nucleotide sequence that encodes a fusion protein comprising all or a portion of APOBEC3C and a detectable heterologous protein that provides for a detectable signal (e.g., luciferase, β-galactosidase, a green fluorescent protein, an epitope tag such as hemagglutinin, and the like), under the control of an APOBEC3C promoter; contacting the cell with the test agent; and detecting the level of APOBEC3C protein by detecting the heterologous protein, using standard assays well known in the art.

Where a subject assay for identifying an agent that reduces the level of active APOBEC3C involves determining the effect of a test agent on the level of APOBEC3C protein that induces a C→U mutation in a lentivirus minus strand, resulting in a G→A mutation in viral reverse transcripts and/or that induces a C→T mutation in a DNA copy, the assay can be conducted in a number of ways. For example, the number of C→U mutations induced in a lentivirus minus strand is determined by detecting polymerase chain reaction (PCR) products amplified using Taq polymerase or Pfu polymerase, using as a template a cDNA copy of a lentivirus RNA produced by a cell in the presence or absence of a test agent. Taq polymerase will copy templates containing uracil; Pfu polymerase does not readily copy templates containing uracil. PCR performed with Taq polymerase will yield a product of the expected size (based on the location of the primers used); while PCR performed with Pfu polymerase will be produced at a much lower level than the Taq-produced product. As another example, PCR products amplified using Taq polymerase and, as template, a cDNA copy of a lentivirus RNA produced by a cell in the presence or absence of a test agent, are sequenced, and the presence of G→A substitutions is detected. Thus, e.g., in some embodiments, the level of active APOBEC3C in a cell is determined by detecting the number of G→A substitutions in a cDNA copy of a lentivirus RNA produced by a cell in the presence or absence of a test agent. Where a test agent reduces the level of active APOBEC3C in a cell, the number of G→A substitutions in a cDNA copy of a lentivirus RNA produced by the cell in the presence of the test agent would be expected to be lower than the number of G→A substitutions in a cDNA copy of a lentivirus RNA produced by the cell in the absence of the test agent.

In some embodiments, the number of APOBEC3C-induced mutations in a lentivirus nucleic acid is determined using an in vitro cytidine deaminase assay. For example, a radiolabeled oligonucleotide substrate for deamination is incubated with test samples lacking or containing APOBEC3C. A suitable substrate contains a target deoxycytidine(s) for APOBEC3C action. APOBEC3C deaminates a cytosine base, converting it to uracil. Uracil is susceptible to the activity of uracil DNA glycosylase (UDG or UNG). Addition of UDG/UNG to the enzymatic reaction results in the removal of the uracil base from the oligonucleotide, creating an abasic lesion at the site of cytidine deamination. The phosphate-sugar backbone of the oligonucleotide at the abasic site is, in turn, susceptible to alkaline hydrolysis. Addition of NaOH to the reaction thus results in cleavage at the site of deamination. Cleavage is monitored by electrophoresis through acrylamide-urea gels, and APOBEC3C activity is thereby scored by the appearance of a shorter cleavage product derived from the longer substrate oligonucleotide, with cleavage occurring specifically at the site of deamination.

Cell-free Screening Methods

In some embodiments, the invention provides cell-free in vitro methods of identifying an agent that reduces enzymatic activity of APOBEC3C. In these embodiments, a subject screening method involves determining the effect of a test agent on the enzymatic activity of APOBEC3C. The method generally involves contacting a sample comprising an APOBEC3C polypeptide and a nucleic acid (e.g., a "target nucleic acid") with a test agent; and determining the effect, if any, of the test agent on the number of mutations induced in the nucleic acid by the APOBEC3C polypeptide. In some embodiments, the method involves contacting a sample comprising the APOBEC3C protein and a nucleic acid with a test agent; and determining the effect, if any, of the test agent on the deaminase activity of the APOBEC3C protein.

A test agent of interest reduces enzymatic activity of APOBEC3C by at least about 10%, at least about 15%, at least about 20%, at least about 25%, at least about 30%, at least about 40%, at least about 50%, at least about 75%, or more, compared to the level of enzymatic activity of APOBEC3C in the absence of the test agent. In some embodiments, a test agent of interest reduces the number of mutations introduced into a nucleic acid by activity of APOBEC3C to less than about 15 mutations per 100 contiguous nucleotides, less than about 10 mutations per 100 contiguous nucleotides, less than about 7 mutations per 100 contiguous nucleotides, less than about 5 mutations per 100 contiguous nucleotides, less than about 3 mutations per 100 contiguous nucleotides, or less than 1 mutation per 100 contiguous nucleotides. Mutations are typically G to A substitutions, but other mutations, e.g., A to G substitutions, are also included.

The APOBEC3C protein can be isolated, purified, or partially purified, e.g., the APOBEC3C protein can be in a cell extract or a cell lysate. In some embodiments, the APOBEC3C is a fusion protein that comprises APOBEC3C and, as a fusion partner, an epitope tag, where the epitope tag is present at the amino terminus of APOBEC3C, at the carboxyl terminus of APOBEC3C, or elsewhere within the APOBEC3C protein. In some of these embodiments, the APOBEC3C-epitope tag fusion protein is used to extract the APOBEC3C protein from a cell lysate.

The target nucleic acid includes nucleotide sequences that are targeted by APOBEC3C, e.g., as described in the Examples. Target nucleic acids may encode, e.g., an HIV-1 protease. Suitable target nucleic acids include, but are not limited to, nucleic acids found under GenBank Accession Nos. AF459117, AY365898.1, and the like, e.g., protease-encoding nucleic acids; and a polynucleotide comprising SEQ ID NO:5.

Determining the effect on the number of mutations induced in the nucleic acid is generally by determining the level of deamination of nucleotide bases in the nucleic acid. Detection of deamination is in some embodiments achieved by treating the nucleic acid with a uracil deglycosylase, and detecting missing bases, as described above. Detection of deamination is in some embodiments achieved by treating the nucleic acid with a uracil deglycosylase, and detecting missing bases using a polymerase chain reaction or a primer extension reaction. In some embodiments, determining the level of deamination of nucleotide bases in the nucleic acid is achieved by contacting the nucleic acid with a detectably labeled nucleic acid probe that binds only if the nucleic acid has not been deaminated. For example, the detectably labeled nucleic acid probe comprises a fluorescent tag, such as fluorescein isothiocyanate, or any of a number of other fluorescent tags that are well known in the art.

Agents

The present invention further provides active agents that reduce the level of active APOBEC3C in a cell; and compositions, including pharmaceutical compositions, comprising the active agent(s). Of particular interest in many embodiments are active agents identified using a screening method of the invention. The subject active agents are useful for reducing the frequency of mutation of a lentivirus, thereby reducing the probability of generating strains that are resistant to treatment with conventional agents, and are therefore useful for treating lentiviral infections. In many embodiments, a subject active agent that reduces APOBEC3C enzymatic activity is co-administered with at least one additional therapeutic agent for treating a lentivirus infection.

In many embodiments, the agent is a small molecule, e.g., a small organic or inorganic compound having a molecular weight of more than 50 and less than about 2,500 daltons. Agents may comprise functional groups necessary for structural interaction with proteins, particularly hydrogen bonding, and may include at least an amine, carbonyl, hydroxyl or carboxyl group, and may contain at least two of the functional chemical groups. The agents may comprise cyclical carbon or heterocyclic structures and/or aromatic or polyaromatic structures substituted with one or more of the above functional groups. Agents are also found among biomolecules including peptides, saccharides, fatty acids, steroids, purines, pyrimidines, derivatives, structural analogs or combinations thereof.

In some embodiments, an active agent is a peptide (e.g., peptide inhibitors of APOBEC3C enzymatic activity). Suitable peptides include peptides of from about 3 amino acids to about 50 amino acids, from about 5 amino acids to about 30 amino acids, from about 10 amino acids to about 25 amino acids, from about 25 amino acids to about 50 amino acids, from about 50 amino acids to about 75 amino acids, or from about 75 amino acids to about 100 amino acids in length. In some embodiments, the peptide is linear; in other embodiments, the peptide is cyclized. In some embodiments, the peptide is modified, e.g., comprises one or more non-peptide moieties covalently or non-covalently linked to the peptide. Suitable non-peptide moieties include, but are not limited to, polyethylene glycol (PEG) moieties; carbohydrate moieties; lipid moieties; fatty acid moieties; polysaccharide moieties; phosphate groups; and the like. In some embodiments, the active peptide is linked to a heterologous peptide, e.g., a heterologous peptide that confers increased stability or residence time in vivo; a heterologous peptide that facilitates crossing a cell membrane; a heterologous peptide that binds to a cell surface receptor; a heterologous peptide that provides for dimerization; a heterologous peptide that provides an epitope tag; a heterologous peptide that provides a detectable signal; and the like.

Peptides can include naturally-occurring and non-naturally occurring amino acids. Peptides may comprise D-amino acids, a combination of D- and L-amino acids, and various "designer" amino acids (e.g., β-methyl amino acids, Cα-methyl amino acids, and Nα-methyl amino acids, etc.) to convey special properties to peptides. Additionally, peptide may be a cyclic peptide. Peptides may include non-classical amino acids in order to introduce particular conformational motifs. Any known non-classical amino acid can be used. Non-classical amino acids include, but are not limited to, 1,2,3,4-tetrahydroisoquinoline-3-carboxylate; (2S,3S)-methylphenylalanine, (2S,3R)-methyl-phenylalanine, (2R,3S)- methyl-phenylalanine and (2R,3R)-methyl-phenylalanine; 2-aminotetrahydronaphthalene-2-carboxylic acid; hydroxy-1,2,3,4-tetrahydroisoquinoline-3-carboxylate; β-carboline (D and L); HIC (histidine isoquinoline carboxylic acid); and HIC (histidine cyclic urea). Amino acid analogs and peptidomimetics may be incorporated into a peptide to induce or favor specific secondary structures, including, but not limited to, LL-Acp (LL-3-amino-2-propenidone-6-carboxylic acid), a β-turn inducing dipeptide analog; β-sheet inducing analogs; β-turn inducing analogs; α-helix inducing analogs; γ-turn inducing analogs; Gly-Ala turn analog; amide bond isostere; tetrazol; and the like.

In some embodiments, an active agent is a short interfering RNA (siRNA), A "small interfering" or "short interfering RNA" or siRNA is a RNA duplex of nucleotides that is targeted to a gene of interest (a "target gene"). An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29 nucleotides, 28 nucleotides, 27 nucleotides, 26 nucleotides, 25 nucleotides, 24 nucleotides, 23 nucleotides, 22 nucleotides, 21 nucleotides, 20 nucleotides, 19 nucleotides, 18 nucleotides, 17 nucleotides, 16 nucleotides, 15 nucleotides, 14 nucleotides, 13 nucleotides, 12 nucleotides, 11 nucleotides, or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5 nucleotides, 6 nucleotides, 7 nucleotides, 8 nucleotides, 9 nucleotides, 10 nucleotides, 11 nucleotides, 12 nucleotides, or 13 nucleotides in length. The hairpin structure can also contain 3' or 5' overhang portions. The 3' or 5' overhang is from 1 nucleotide to about 100 nucleotides in length, e.g., from about 1 nucleotide to about 5 nucleotides, from about 5 nucleotides to about 10 nucleotides, from about 10 nucleotides to about 15 nucleotides, from about 15 nucleotides to about 20 nucleotides, from about 20 nucleotides to about 25 nucleotides, from about 25 nucleotides to about 30 nucleotides, from about 30 nucleotides to about 40 nucleotides, from about 40 nucleotides to about 50 nucleotides, from about 50 nucleotides to about 60 nucleotides, from about 60 nucleotides to about 75 nucleotides, or from about 75 nucleotides to about 100 nucleotides in length. In some embodiments, the overhang is a 3' or a 5' overhang 1 nucleotides, 2 nucleotides, 3 nucleotides, 4 nucleotides, or 5 nucleotides in length.

Interfering RNA (RNAi) fragments, particularly double-stranded (ds) RNAi, can be used to inhibit gene expression. One approach well known in the art for inhibiting gene expression is short interfering RNA (siRNA) mediated gene silencing, where the level of expression product of a target gene is reduced by specific double stranded siRNA nucleotide sequences that are complementary to at least a 19-25 nucleotide long segment (e.g., a 20-21 nucleotide sequence) of the target gene transcript, including the 5' untranslated (UT) region, the ORF, or the 3' UT region. In some embodiments, short interfering RNAs are about 19-25 nt in length. See, e.g., PCT applications WO0/44895, WO99/32619, WO01/75164, WO01/92513, WO01/29058, WO01/89304, WO02416620, and WO02/29858; U.S. Patent Publication No. 20040023390; and U.S. Patent Publication No. 20040086884 for descriptions of siRNA technology. The siRNA can be encoded by a nucleic acid, and the nucleic acid can also include a promoter operably linked to the siRNA-encoding nucleic acid. The nucleic acid sequence can also include a polyadenylation signal. In some embodiments, the polyadenylation signal is a synthetic minimal polyadelylation signal.

"Inhibition of gene expression" refers to the absence (or detectable decrease) in the level of protein and/or mRNA product from a APOBEC3C gene, where a dsRNA that controls expression of a target gene reduces translation of the APOBEC3C mRNA by at least about 10%, at least about 20%, at least about 30%, at least about 50%, at least about 75%, or more, compared to the level of translation of the APOBEC3C mRNA in the absence of the dsRNA.

In some embodiments, an siRNA inhibits production of APOBEC3C protein; and does not substantially inhibit production of any other host deaminase. In other embodiments, an siRNA inhibits production of both APOBEC3C protein and APOBEC3F protein; and does not substantially inhibit production of any other host deaminase. In other embodiments, an siRNA inhibits production of both APOBEC3C protein and APOBEC3F protein; and inhibits production of at least one other host deaminase, e.g., at least one additional APOBEC protein. In some embodiments, an siRNA inhibits production of APOBEC3F protein; and does not substantially inhibit production of any other host deaminase.

Treatment Methods

The present invention provides treatment methods, including methods of treating a lentivirus infection, preventing lentivirus infection, reducing the emergence of drug-resistant strain of lentivirus, reducing the incidence of mutation in a lentivirus genome, reducing the probability of lentivirus infection, reducing the incidence of viral escape from a host immune response, reducing the spread of lentivirus from an infected cell to a susceptible cell, reducing viral load in an lentivirus-infected individual, reducing an amount of virally-encoded polypeptide(s) in an lentivirus-infected individual, and increasing $CD4^+T$ cell count in an lentivirus-infected individual. The methods generally involve administering to an individual in need of such therapy an effective amount of an agent that reduces the level of active host deaminase in a cell in the individual, where the cell includes is one that is infected with a lentivirus. In some embodiments, an agent that inhibits a host deaminase enzyme is administered as monotherapy. In other embodiments, an agent that inhibits a host deaminase is administered in combination therapy with at least one additional therapeutic agent.

An agent that inhibits a host deaminase enzyme and that is suitable for use in a subject method, is an agent that inhibits one or more of APOBEC3C, APOBEC3F, and an ADAR adenosine deaminase (e.g., RNA-specific adenosine deaminase). A host deaminase enzyme that is a target of inhibition in a subject method is an enzyme that induces mutations in a lentivirus genome. In some embodiments of particular interest, an agent is one that inhibits APOBEC3C activity. In some embodiments of particular interest, an agent is one that inhibits APOBEC3F activity. In other embodiments of particular interest, an agent is one that inhibits both APOBEC3C and APOBEC3F activity. Inhibition of a host deaminase activity can be through direct inhibition of the active site of the enzyme; through allosteric inhibition; through a reduction in synthesis of the enzyme; and the like.

In some embodiments, an agent that inhibits a host deaminase enzyme is an agent that selectively inhibits only one host deaminase enzyme; and does not substantially inhibit other host deaminase enzymes. For example, in some embodiments, an agent that inhibits a host deaminase enzyme is an agent that selectively inhibits APOBEC3C deaminase activity; and does not substantially inhibit any other host deaminase enzyme. In other embodiments, an agent that inhibits a host deaminase enzyme is an agent that selectively inhibits two or more related host deaminase enzymes; and does not substantially inhibit other host deaminase enzymes. For example, in some embodiments, an agent that inhibits a host deaminase enzyme is an agent that selectively inhibits APOBEC3C and APOBEC3F deaminase activity; and does not substantially inhibit any other host deaminase enzyme.

An agent that inhibits a host deaminase enzyme, and that is suitable for use in a subject method, inhibits a host deaminase activity by at least about 10%, at least about 20%, at least about 25%, at least about 30%, at least about 40%, at least about 50%, at least about 60%, at least about 70%, at least about 80%, or at least about 90%, or more, compared to the level of enzymatic activity of the host-deaminase in the absence of treatment with the agent.

Methods of Reducing the Incidence of Mutation in a Lentivirus Genome

The present invention provides methods of reducing the mutation rate of a lentivirus in a cell; method of reducing the incidence of mutation in lentivirus genome; methods of reducing the emergence of drug-resistant strains of lentivirus; and methods of reducing the emergence of variant lentivirus strains that evade host immune responses. The present invention provides methods of reducing the incidence of a mutation in a lentivirus. The methods generally involve administering to an individual who is infected with a lentivirus an effective amount of an agent that inhibits a host deaminase enzyme. The agent enters a cell that is infected with a lentivirus, and reduces the level of active host deaminase in the cell. In some embodiments, an agent that inhibits a host deaminase enzyme is administered as monotherapy. In other embodiments, an agent that inhibits a host deaminase is administered in combination therapy with at least one additional therapeutic agent.

An agent that inhibits a host deaminase enzyme, and that is suitable for use in a subject method, reduces the incidence of mutation in a lentivirus genome by at least about 10%, at least about 20%, at least about 25%, at least about 30%, at least about 40%, at least about 50%, at least about 60%, at least about 70%, at least about 80%, or at least about 90%, or more, compared to the incidence of mutation in the lentivirus genome in the absence of treatment with the agent.

Whether an agent reduces the incidence of a mutation in a lentivirus genome is readily determined by one or more of: a) determining the nucleotide sequence of a lentivirus (or a portion of a lentivirus, e.g., a coding region) obtained from an infected individual; and comparing the nucleotide sequence with the nucleotide sequence of a wild-type lentivirus, or with the nucleotide sequence of a lentivirus (or a portion of a lentivirus, e.g., a coding region) obtained from the same individual at an earlier time point; b) determining the incidence of escape of a lentivirus in the host from a host immune response; and c) determining the incidence of resistance of a lentivirus in the host to an anti-lentivirus therapeutic agent. In some embodiments, the incidence of a mutation in a lentivirus genome is determined by comparing the nucleotide sequence of a lentivirus (or a portion of a lentivirus, e.g., a coding region) obtained from an infected individual at a second time point; and comparing the nucleotide sequence with the nucleotide sequence of a lentivirus (or a portion of a lentivirus, e.g., a coding region) obtained from the same individual at a first time point, which second time point is later than the first time point, e.g., the second time point is from about 2 weeks to about 2 years after the first time point.

In some embodiments, an agent that inhibits a host deaminase enzyme reduces the incidence of mutation in a lentivirus reverse transcriptase inhibitor, a lentivirus-encoded protease, an envelope gp120 protein, an envelope gp41 protein, Vif, a lentivirus-encoded integrase, and a lentivirus Gag protein.

In some embodiments, an agent that, inhibits a host deaminase enzyme reduces the incidence of mutation in a lentivirus genome, which mutation is one that results in viral escape of a host immune response (e.g., a host antibody response and/or a host cytotoxic T cell (CTL) response). Thus, in some embodiments, an agent that inhibits a host deaminase enzyme reduces escape of the lentivirus from a host immune response, e.g., a host humoral (e.g., antibody) and/or a host CTL response.

Methods of Treating a Lentivirus Infection

The present invention provides methods of treating a lentivirus infection in an individual. In some embodiments, the methods generally involve administering to an individual having a lentivirus infection, or at risk of having a lentivirus infection, an effective amount of an active agent that reduces the level of active host deaminase in a cell in the individual. In some embodiments, the methods generally involve administering to an individual having a lentivirus infection, or at risk of having a lentivirus infection, an effective amount of an active agent that reduces the level of APOBEC3C activity in a cell (e.g., reduces the level of APOBEC3C mRNA, and/or reduces the level of APOBEC3C protein, and/or reduces APOBEC3C enzymatic activity).

In many embodiments, a subject method reduces the number of mutations introduced into a lentivirus, or a lentivirus population, in an individual. In many embodiments, a subject method reduces the probability that a drug-resistant lentivirus will emerge in the individual being treated. Thus, in many embodiments, a subject method increases the sensitivity of a lentivirus to treatment with at least a second anti-lentivirus agent.

Treating a lentivirus infection, includes, but is not limited to, preventing lentivirus infection, reducing the emergence of drug-resistant strain of lentivirus, reducing the probability of lentivirus infection, reducing the incidence of viral escape from a host immune response, reducing the spread of lentivirus from an infected cell to a susceptible cell, reducing viral load in an lentivirus-infected individual, reducing an amount of virally-encoded polypeptide(s) in an lentivirus-infected individual, and increasing CD4$^+$T cell count in an lentivirus-infected individual.

The amount of subject agent which is administered will vary with the nature of the drug. As one non-limiting example, a subject agent can be administered in the range of about 0.2 mg/kg/day to about 20 mg/kg/day. The determination of how large a dose is to be used may be determined using an animal model (e.g., a non-human primate model) and relating the dosage based on pharmacokinetics, e.g. with equations predictive of interspecies scaling. Usually, the lowest effective dose will be used.

Any of a variety of methods can be used to determine whether a treatment method is effective. For example, methods of determining whether the methods of the invention are effective in reducing lentivirus load, increasing sensitivity of the lentivirus to treatment with at least a second anti-lentivirus agent, and/or reducing emergence of a drug-resistant lentivirus strain, and/or treating an lentivirus infection, are any known test for indicia of lentivirus infection, including, but not limited to, measuring viral load, e.g., by measuring the amount of lentivirus in a biological sample, e.g., using a polymerase chain reaction (PCR) with primers specific for a lentivirus polynucleotide sequence; detecting and/or measuring a polypeptide encoded by lentivirus, e.g., p24, gp120, reverse transcriptase, using, e.g., an immunological assay such as an enzyme-linked immunosorbent assay ELISA) with an antibody specific for the polypeptide; measuring the number of mutant lentivirus in a population of lentivirus in an individual; and measuring the $CD4^+T$ cell count in the individual.

Methods of assaying an lentivirus infection (or any indicia associated with an lentivirus infection) are known in the art, and have been described in numerous publications such as *HIV Protocols* (*Methods in Molecular Medicine,* 17) N. L. Michael and J. H. Kim, eds. (1999) Humana Press.

In some embodiments, a subject method involves administering an agent that inhibits a first host deaminase, or a first set of host deaminases, during an early, pre-clinical (e.g., before the emergence of symptoms associated with a lentivirus infection) stage of lentivirus infection; and administering an agent that inhibits a second host deaminase (or a second set of host deaminases) at a later stage of lentivirus infection (e.g., a stage in which the individual exhibits one or more symptoms associated with a lentivirus infection). The first host deaminase differs from the second host deaminase. Likewise, the first set of host deaminases differs from the second set of host deaminases. The first set of host deaminases may or may not be overlapping with the second set of host deaminases.

For example, in some embodiments, a subject method involves administering an agent that inhibits a first host deaminase, or a first set of host deaminases, to an individual who is infected with a lentivirus, and who has a $CD4^+T$ cell count in a range of from about 420 $CD4^+$-T cells/mm$^3$ blood to about 1500 $CD4^+$-T cells/mm$^3$ blood; then administering an agent that inhibits or increases the activity of a second host deaminase (or a second set of host deaminases) at a later stage, e.g., when the individual has a $CD4^+T$ cell count of less than about 420 $CD4^+$-T cells/mm$^3$ blood.

Formulations, Dosages, and Routes of Administration

In general, an active agent (e.g., an agent that reduces APOBEC3C enzymatic activity; an agent that reduces the frequency or emergence of drug-resistant strains of lentivirus; etc.) is prepared in a pharmaceutically acceptable composition for delivery to a host. The terms "active agent," "drug," "agent," "therapeutic agent," and the like are used interchangeably herein. Pharmaceutically acceptable carriers preferred for use with a subject agent may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, and microparticles, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. A composition comprising a subject agent may also be lyophilized using means well known in the art, for subsequent reconstitution and use according to the invention.

Formulations

An active agent (e.g., an agent that reduces APOBEC3C enzymatic activity; an agent that reduces the frequency or emergence of drug-resistant strains of lentivirus; etc.) is administered to an individual in need thereof in a formulation with a pharmaceutically acceptable excipient(s). A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

In the subject methods, an active agent may be administered to the host using any convenient means capable of resulting in the desired reduction in APOBEC3C enzymatic activity. Thus, an active agent can be incorporated into a variety of formulations for therapeutic administration. More particularly, an active agent can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, an active agent may be administered in the form of its pharmaceutically acceptable salts, or it may also be used alone or in appropriate association, as well as in combination, with other pharmaceutically active compounds. The following methods and excipients are merely exemplary and are in no way limiting.

For oral preparations, an active agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An active agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. An active agent can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more active agents. Similarly, unit dosage forms for injection or intravenous administration may comprise the active agent(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of an active agent, calculated in an amount sufficient to produce the desired effect in association with a pharmaceutically acceptable diluent, carrier or vehicle. The specifications for a given active agent will depend in part on the particular agent employed and the effect to be achieved, and the pharmacodynamics associated with each compound in the host.

Other modes of administration will also find use with the subject invention. For instance, an active agent can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

An active agent can be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

An active agent will in some embodiments be formulated for vaginal delivery. A subject formulation for intravaginal administration is formulated as an intravaginal bioadhesive tablet, intravaginal bioadhesive microparticle, intravaginal cream, intravaginal lotion, intravaginal foam, intravaginal ointment, intravaginal paste, intravaginal solution, or intravaginal gel.

A subject formulation comprising an active agent includes one or more of an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrrolidone or aluminum stearate), a dispersing agent (e.g., hydroxypropylmethylcellulose), a diluent (e.g., water), and base wax (e.g., cocoa butter, white petrolatum or polyethylene glycol).

Tablets comprising an active agent may be coated with a suitable film-forming agent, e.g., hydroxypropylmethyl cellulose, hydroxypropyl cellulose or ethyl cellulose, to which a suitable excipient may optionally be added, e.g., a softener such as glycerol, propylene glycol, diethylphthalate, or glycerol triacetate; a filler such as sucrose, sorbitol, xylitol, glucose, or lactose; a colorant such as titanium hydroxide; and the like.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosages

Although the dosage used will vary depending on the clinical goals to be achieved, a suitable dosage range is one which provides up to about 1 µg to about 100 mg, e.g., from about 1 µg to about 25 µg, from about 25 µg to about 50 µg, from about 50 µg to about 100 µg, from about 100 µg to about 250 µg, from about 250 µg to about 500 µg, from about 500 µg to about 1 mg, from about 1 mg to about 25 mg, from about 25 mg to about 50 mg, or from about 50 mg to about 100 mg, of an active agent can be administered in a single dose. Alternatively, a target dosage of an active agent can be considered to be about in the range of about 0.1-1000 µM, about 0.5-500 µM, about 1-100 µM, or about 5-50 µM in a sample of host blood drawn within the first 24-48 hours after administration of the agent.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

In some embodiments, a single dose of an active agent is administered. In other embodiments, multiple doses of an active agent are administered. Where multiple doses are administered over a period of time, an active agent is administered twice daily (qid), daily (qd), every other day (qod), every third day, three times per week (tiw), or twice per week (biw) over a period of time. For example, an active agent is administered qid, qd, qod, tiw, or biw over a period of from one day to about 2 years or more. An active agent is administered at any of the aforementioned frequencies for one week, two weeks, one month, two months, six months, one year, or two years, or more, depending on various factors. In some embodiments, the agent is administered for a period of time of from about 2 years to about 50 years (or more), e.g., from about 2 years to about 5 years, from about 5 years to about 10 years, from about 10 years to about 20 years, from about 20 years to about 30 years, from about 30 years to about 40 years, or from about 40 years to about 50 years, or more.

Routes of Administration

An active agent is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, intratumoral, transdermal, subcutaneous, intradermal, topical application, intravenous, vaginal, nasal, and other parenteral routes of administration. Suitable routes of administration also include oral and rectal routes. Routes of administration may be combined, if desired, or adjusted depending upon the agent and/or the desired effect. The composition can be administered in a single dose or in multiple doses.

An active agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, vaginal, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The agent can also be delivered to the subject by enteral administration. Enteral routes of administration include, but are not necessarily limited to, oral and rectal (e.g., using a suppository) delivery.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as the number of viral particles per unit blood. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts (wherein the term "host" is used interchangeably herein with the terms "subject" and "patient") are treatable according to the subject methods. Generally such hosts are "mammals" or "mammalian," where these terms are used broadly to describe organisms which are within the class mammalia, and primates (e.g., humans, chimpanzees, and monkeys), that are susceptible to lentivirus infection. In many embodiments, the hosts will be humans.

Combination Therapies

A subject agent can be administered to an individual in combination (e.g., in the same formulation or in separate formulations) with at least a second therapeutic agent ("combination therapy"). The subject agent can be administered in admixture with a second therapeutic agent or can be administered in a separate formulation. When administered in separate formulations, a subject agent and a second therapeutic agent can be administered substantially simultaneously (e.g., within about 60 minutes, about 50 minutes, about 40 minutes, about 30 minutes, about 20 minutes, about 10 minutes, about 5 minutes, or about 1 minute of each other) or separated in time by about 1 hour, about 2 hours, about 4 hours, about 6 hours, about 10 hours, about 12 hours, about 24 hours, about 36 hours, or about 72 hours, or more. Effective amounts of a therapeutic agent are as described above.

Therapeutic agents that can be administered in combination therapy, include, but are not limited to, anti-inflammatory agents, anti-viral agents, anti-fungal agents, anti-mycobacterial agents, antibiotic agents, amoebicidal agents, trichomonocidal agents, analgesic agents, anti-neoplastic agents, anti-hypertensive agents, anti-microbial agents and/or steroid drugs. In some embodiments, patients with a viral, fungal, or bacterial infection are treated with a combination of one or more subject agents with one or more of the following; beta-lactam antibiotics, tetracyclines, chloramphenicol, neomycin, gramicidin, bacitracin, sulfonamides, nitrofirazone, nalidixic acid, cortisone, hydrocortisone, betametasone, dexamethasone, fluocortolone, prednisolone, triamcinolone, indomethacin, sulindac, acyclovir, amantadine, rimantadine, recombinant soluble CD4 (rsCD4), anti-receptor antibodies (e.g., for rhinoviruses), nevirapine, cidofovir (Vistide™), trisodium phosphonoformate (Foscarnet™), farncyclovir, pencyclovir, valacyclovir, nucleic acid/replication inhibitors, interferon, zidovudine (AZT, Retrovir™), zidovudine/lamivudine (Combivir), didanosine (dideoxyinosine, ddI, Videx™), stavudine (d4T, Zerit™), zalcitabine (dideoxycytosine, ddC, Hivid™), nevirapine (Viramune™), lamivudine (Epivir™, 3TC), protease inhibitors, saquinavir (Invirase™, Fortovase™), ritonavir (Norvir™), nelfinavir (Viracept™), efavirenz (Sustiva™), abacavir (Ziagen™), amprenavir (Agenerase™) indinavir (Crixivan™), ganciclovir, AzDU, delavirdine (Rescriptor™), lopinavir/ritonavir (Kaletra), tenofovir, emtricitabine, Enfurvitide (Fuzeon, T-20), trizivir, rifampin, clathiromycin, erythropoietin, colony stimulating factors (G-CSF and GM-CSF), non-nucleoside reverse transcriptase inhibitors, nucleoside inhibitors, fusion inhibitors, adriamycin, fluorouracil, methotrexate, asparaginase and combinations thereof. Additional antiviral agents that are suitable for use in combination therapy include, but are not limited to, nucleotide and nucleoside analogs. Non-limiting examples include azidothymidine (AZT) (zidovudine), and analogs and derivatives thereof; 2',3'-dideoxyinosine (ddI) (didanosine), and analogs and derivatives thereof; 2',3'-dideoxycytidine (ddC) (dideoxycytidine), and analogs and derivatives thereof; 2'3'-didehydro-2',3'-dideoxythymidine (d4T) (stavudine); tenofovir disoproxil fumarate (tenofovir DF); cis-1-[2'-hydroxymethyl-5'-(1,3-oxathiolanyl)]cytosine (3TC); (−)-2',3'-Dideoxy-5-fluoro-3'-thiacytidine (FTC); and analogs and derivatives of any of the foregoing. Anti-HIV agents are those in the preceding list that specifically target a unction of one or more HIV proteins.

In some embodiments, a subject agent is administered in combination therapy with two or more anti-HIV agents. For example, a subject agent can be administered in combination therapy with one, two, or three nucleoside reverse transcriptase inhibitors (e.g., Combivir (AZT+3TC), Epivir (3TC), Emtriva (FTC), Epzicom (abacavir+3TC), Hivid (ddC), Retrovir (AZT), Trizivir (AZT+abacavir+3TC), Truvada (tenofovir DF+FTC), Videx (ddI), Viread (tenofovir DF), Zerit (d4T), Ziagen (abacavir), etc.). A subject agent can be administered in combination therapy with one or two non-nucleoside reverse transcriptase inhibitors (e.g., Rescriptor (delavirdine), Sustiva (efavirenz), Viramune (nevirapine), etc.). A subject agent can be administered in combination therapy with one or two protease inhibitors (e.g., Agenerase (amprenavir), Crixivan (indinavir), Fortovase (saquinavir), Invirase (saquinavir), Kaletra (lopinavir+ritonavir), Norvir (ritonavir), Lexiva (fosamprenavir) Viracept (nelfinavir), Reyataz (atazanavir), etc.).

A subject agent can be administered in combination therapy with a protease inhibitor and a nucleoside reverse transcriptase inhibitor. A subject agent can be administered in combination therapy with a protease inhibitor, a nucleoside reverse transcriptase inhibitor, and a non-nucleoside reverse transcriptase inhibitor. A subject agent can be administered in combination therapy with a protease inhibitor and a non-nucleoside reverse transcriptase inhibitor. Other combinations of a subject inhibitor with one or more of a protease inhibitor, a nucleoside reverse transcriptase inhibitor, and a non-nucleoside reverse transcriptase inhibitor are contemplated.

In some embodiments, an agent that reduces a level of active APOBEC3C is co-administered with at least one protease inhibitor. For example, in some embodiments, an agent that reduces a level of active APOBEC3C is co-administered with one or more of amprevanir, indinavir, saquinavir, lopinavir, ritonavir, a combination or lopinavir and ritonavir, fosamprenavir, atazanavir, and nelfinavir. Amprenavir is typically administered in an amount of 1200 mg, administered orally twice daily. Indinavir is typically administered in an amount of 800 mg, administered orally every eight hours, for a total of 2400 a day. Saquinavir is typically administered in an amount of 600 mg, administered orally three times daily. Fosamprenavir is typically administered in an amount of 1400 mg, administered orally twice daily. Ritonavir is typically administered in an amount of 600 mg, administered orally twice daily. Atazanavir is typically administered in an amount of 400 mg, administered orally once daily, Nelfinavir is typically administered in an amount of 1250 mg, administered orally twice daily.

In some embodiments, an agent that reduces a level of active APOBEC3C is co-administered with at least one non-nucleoside reverse transcriptase inhibitor. For example, in some embodiments, an agent that reduces a level of active APOBEC3C is co-administered with one or more of delavirdine, efavirenz, and nevirapine. Typically, delavirdine is administered in an amount of 400 mg, administered orally three times a day. Typically, efavirenz is administered in an amount of 600 mg, administered orally once daily. Typically, nevirapine is administered in an amount of 200 mg, administered orally once per day for 14 days, then twice per day thereafter.

In some embodiments, an agent that reduces a level of active APOBEC3C is co-administered with at least one nucleoside reverse transcriptase inhibitor. For example, in some embodiments, an agent that reduces a level of active APOBEC3C is co-administered with one or more of: a combination of retrovir and epivir; 3TC; FTC; a combination of 3TC and abacavir; ddC; AZT; a combination of AZT, abacavir, and 3TC; a combination of tenofovir DF and FTC; ddI; tenofovir DF; d4T; and abacavir. Typically, 3TC is administered in an amount of 300 mg, administered orally once daily, or 150 mg, administered orally twice daily. Typically, FTC is administered in an amount of 200 mg, administered orally once daily. Typically, ddC is administered in an amount of 0.75 mg, administered orally three times daily. Typically, AZT is administered in an amount of 300 mg, administered twice daily. Typically, ddI is administered in an amount of 200 mg, administered orally twice daily. Typically tenofovir DF is administered in an amount of 300 mg, administered orally once daily. Typically, d4T is administered in an amount of 40 mg, administered orally twice daily. Typically, abacavir is administered in an amount of 300 mg, administered orally twice daily.

Kits, Containers, Devices, Delivery Systems

Kits with unit doses of the active agent, e.g. in oral, vaginal, rectal, transdermal, or injectable doses (e.g., for intramuscular, intravenous, or subcutaneous injection), are provided. In such kits, in addition to the containers containing the unit doses will be an informational package insert describing the use and attendant benefits of the drugs in treating a lentivirus infection, e.g., an HIV infection, Suitable active agents and unit doses are those described herein above.

In many embodiments, a subject kit will further include instructions for practicing the subject methods or means for obtaining the same (e.g., a website URL directing the user to a webpage which provides the instructions), where these instructions are typically printed on a substrate, which substrate may be one or more of: a package insert, the packaging, formulation containers, and the like.

In some embodiments, a subject kit includes one or more components or features that increase patient compliance, e.g., a component or system to aid the patient in remembering to take the active agent at the appropriate time or interval. Such components include, but are not limited to, a calendaring system to aid the patient in remembering to take the active agent at the appropriate time or interval, Subjects Suitable for Treatment The methods of the present invention are suitable for treating individuals who have a lentiviral infection; who are at risk of contracting a lentiviral infection; and who were treated for a lentiviral infection, but who relapsed. Such individuals include, but are not limited to, individuals with healthy, intact immune systems, but who are at risk for becoming HIV infected ("at-risk" individuals). At-risk individuals include, but are not limited to, individuals who have a greater likelihood than the general population of becoming HIV infected. Individuals at risk for becoming HIV infected include, but are not limited to, individuals at risk for HIV infection due to sexual activity with HIV-infected individuals; intravenous drug users; individuals who may have been exposed to HIV-infected blood, blood products, or other HIV-contaminated body fluids; and babies who are being nursed by HIV-infected mothers. Individuals suitable for treatment include individuals infected with, or at risk of becoming infected with, HIV-1 and/or HIV-2 and/or HIV-3, or any variant thereof.

Individuals suitable for treatment with the methods of the invention also include individuals who have a lentiviral infection that is refractory to treatment with other anti-viral therapies.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

APOBEC3C Induces Non-Lethal Hypermutation in HIV-1

Experimental Procedures

Cells and Viruses

H9, CEMSS, SupT1, Magi and 293T cell lines were obtained from the NIH Repository Program. All cell lines were maintained under standard conditions. Peripheral blood mononuclear cells (PBMC) were isolated from healthy donors using Ficoll isolation (Amersham Pharmacia) and were stimulated with 5 µg/ml of PA (phytohemagglutinin) and maintained in medium supplemented with IL-2 prior to infection.

Virus stocks were generated from an infectious molecular clone of HIV-1 subtype β isolate NL4-3 (GenBank M19921) obtained from NIH Program. 210W is a molecular clone having the backbone of NL4-3 and the genes gag and protease derived from a patient who had developed resistance mutations to ritronavir four weeks after treatment. NL43 ΔVif is an NL4-3 variant with three stop codons introduced in the vif gene by directed mutagenesis. ΔEnv NL4-3, Δvif and 210W viruses were generated by digesting each plasmid by Nhe1 restriction enzyme (Invitrogen). The DNA polymerase I Klenow fragment (Biolabs) was used to fill-in the ends, and the plasmids were religated using the T4 DNA ligase (Promega). Pseudotyped VSV-G ΔEnv NL4-3. ΔVif and 210W viruses were produced by cotransfecting 293T with the pMD.G plasmid expressing the VSV-G envelope protein and the plasmid expressing ΔEnv HIV-1 viruses, respectively.

HIV-1 Replication and Infectivity

Stocks of viruses were prepared by transfection of 293T cells. Enzyme-linked immunosorbent assay (ELISA) was used to quantify p24 Gag (Perkin Elmer). Spreading infections were initiated with stocks normalized for p24 Gag levels, the cells were passaged, and replication was monitored over time as the accumulation of p24 Gag in the culture supernatants. Single-cycle infectivity was determined by challenging the cell lines ($5 \times 10^5$ cells) with VSV-G ΔEnv pseudotyped viruses for 24 h.

APOBEC Plasmid Construction

PolyA+ RNA were isolated from H9 cells. APOBEC3C ("h3C"), APOBEC3F ("h3F") and APOBEC3G ("h3G") open reading frames (ORFs) were amplified by reverse transcription-polymerase chain reaction (RT-PCR) using the following primers:

```
3C Fw   ATGAATCCACAGATCAGAAACC;        (SEQ ID NO: 12)

3C Rev  TCACTGGAGACTCTCCCGTA;          (SEQ ID NO: 13)

3F Fw   ATGAAGCCTCACTTCAGAAAC;         (SEQ ID NO: 14)

3F Rev  TCACTCGAGA ATCTCCTGC;          (SEQ ID NO: 15)

3G Fw   ATGAAGCCTCACTTCAGAAACACAG;     (SEQ ID NO: 16)
and

3G Rev  TCAGTTTTCC TGATTCTGGA          (SEQ ID NO: 17)
        GAATGG,
``` where "3C Fw" and "3C Rev" are the forward primer and reverse primer, respectively, for APOBEC3C; where "3F Fw" and "3F Rev" are the forward primer and reverse primer, respectively, for APOBEC3F; and where "3G Fw" and "3G Rev" are the forward primer and reverse primer, respectively, for APOBEC3G.

The amplicons were cloned into pGEM-T easy vectors (Promega) and confirmed by sequencing. The h3C gene with HA tag sequence at its 3' terminus was amplified from mRNA of H9 cells by RT-PCR, using the following primers:

```
3C-Fw-BamH1
                                       (SEQ ID NO: 18)
CGC GGATCC(BamH1 seq)GCCGCCACC(Kozak seq) ATGAATCC
ACAGATCAGAAACC(h3C seq);
and 3C-Rev-HA-Xba1
                                       (SEQ ID NO: 19)
TGCTCTAGA(Xba1 seq)CTAGAGGCTAGCGTAATCCGGAACATCGTAT
GGGTA(HA seq)CTGGAGACTCTCCCGTAGCC(3C seq),
``` and the identity of the product was confirmed by sequencing. It was then cloned for protein expression into PPT-IRES-GFP plasmid using the cloning site BamH1 and Xbal.

Transfection

The 293T or Magi cells were transfected using Lipofectamine 2000 transfection reagent (Invitrogen) according to the manufacture's recommendations. The SupT1 cells were transfected by Amaxa electroporation technology with the program 129.

Nucleic Acid Isolation, PCR, DNA Sequencing and Cell DNA Fingerprinting

DNA was extracted from infected cells with the DNA Easy DNA extraction kit (invitrogen) and quantified by spectrometry. PolyA+RNA were isolated using the QuickPrep Micro mRNA Purification Kit (Pharmacia). PCR was performed with the primers Hypa 10 and Hypa 11 and DP 16 and DP 17 as described previously (Janini et al. ((2001) *J Virol* 75:7973-7986) using approximately 150 ng of DNA. The PCR was performed with Easy-A High Fidelity PCR Cloning Enzyme (Stratagene). The PCR products were sequenced using ABI 3100 technology. DNA fingerprinting of the different cell lines used was checked by allele specific primers (Research Genetics), Western Blot Analysis The detection of APOBEC3C protein expression in 293T transfected cells was performed by western blot using the HA-probe (Y-11) horse radish peroxidase (HRP)-labeled polyclonal antibody specific for the HA tag (Santa Cruz Biotechnology).

RNAi Assay siRNAs targeting h3C from position 167 to position 185 bases relative to the start codon were in vitro transcribed (RiboMax kit, Promega) from a DNA template containing the T7 promoter synthesized by Invitrogen. The sequence of the scrambled RNA was generated using the Promega siRNA target designer.

For the siRNA transfection, 293T cells were seeded into 6-well plates at a density of $10^4$ cells/ml. After about 2 h, purified APOBEC3C siRNAs along with RNA oligonucleotide ("oligo") conjugated to fluorescein isothiocyanate (FITC) (Block It™ kit, Invitrogen) were cotransfected into the cells with Lipofectamine 2000 according to the manufacturer's protocols. A scrambled siRNA along with the RNA oligo conjugated to FITC were cotransfected separately as a control.

The efficiency of transfection was monitored by fluorescent microscopy at 24 h, 48 h and 72 h after siRNA transfection. For flow cytometry analysis, the cells were analyzed using a Becton Dickinson fluorescence activated cell sorter (FACS). Samples were counted, and analyzed with Flowjo software. Non-transfected 293T cells were used as a control. FITC positive cells were sorted (DIVA instrument of Becton Dickinson) for further analysis and infection.

Results

G to A Hypermutation of Wild-Type Virus in PBMC and Different Cell Lines

The 210W and NL4-3 were used to assess if non-lethal hypermutation occurs after infection of cells expressing different deaminases. The products of transfection of 293T cells were confirmed to match plasmid DNA sequences. The viral stocks were used to infect PBMC and, CEMSS and SupT1 cell lines. The identity of the target cells was established by DNA fingerprinting. DNA was isolated 5 days after infection, at which time at least 75% of the cells express intracellular p24. Both 210W and NL4-3 were infectious in all three cell types (FIG. 1).

G to A Hypermutation of Wild-Type Virus in PBMC and Different Cell Lines 210W viral protease DNA from infected cells was amplified using 150 ng of DNA. Population sequencing of the protease amplicons showed that G to A hypermutation occurred in 210W infections of PBMC, H9 cells, CEMSS, 293T, and MAGI, but not SupT1 cells (FIG. 2A). The absence of hypermutation in the SupT1 cell line despite comparable levels of viral replication (FIG. 1) indicates that the G to A hypermutation is not caused by an error prone RT and that hypermutation is cell specific.

FIG. 1. Replication of NL4-3 and 210W in three cell types. The infectivity of 210W in each cell was expressed as a percentage of p24 value of NL4-3 infecting the same cell type in the same experiment. The results presented are the average and the standard deviations (error bars) of at least three independent infection experiments.

Figure 2B:
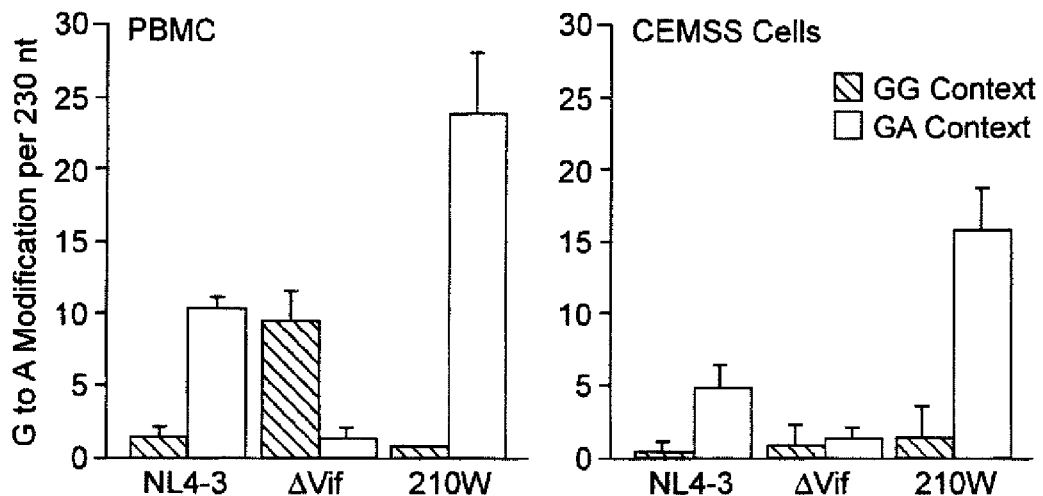

Context Preference of Hypermutation in Wild-Type and Mutant Virus on Different Cells G to A hypermutation is associated with a preference for the dinucleotide context decreasing in the order GA>GG>GT>GC (Fitzgibbon et al. (1993) *AIDS Res Hum Retroviruses* 9:833-838; and Vartanian et al. (1991) *J Virol* 65:1779-1788). To further characterize the pattern of the G to A changes, the context of mutation in the different cells was analyzed. HIV-1 virus stocks NL4-3, NL4-3Δvif, and 210W, were generated in 293T cells by transfection. The three viruses were used for the infection of PBMC and the cell lines CEMSS, and SupT1. 293T and Magi cells were analyzed after a single round infection with pseudotyped 210W, NL4-3 and NL4-3 Δvif. The sequence and the dinucleotide context of G to A mutations in the protease reading frame were analyzed. Although the GA and the GG context were both used in almost every mutated sequence, the trend for preferential mutation of G in the GA context or in the GG context is cell line-specific and virus-specific (FIG. 2B). In the case of 210W virus, in all the cell types analyzed, the numbers of G bases replaced by A in the dinucleotide GA context was at least fifteen fold higher than the number of G replaced by A in the GG context (FIG. 2). G to A substitutions in the GC and GT dinucleotide contexts have been described (Vartanian et al. (1991) supra) and were rare in these experiments. Mutations in NL4-3 had the same GA context preference as 210W, but occurred at a much lower rate. The level of G to A transitions in NL43 Δvif occurred frequently in the GG context in PBMC, which are known to express APOBEC3G, but rarely in CEMSS. The overall frequency of G to A changes in the GA context was low in cell lines that do not express APOBEC3G, including CEMSS, 293T, and Magi cells (FIG. 3). The presence of G to A mutations in CEMSS, 293T and Magi cell lines, which do not express h3G and h3F raises the possibility that another APOBEC deaminase activity is present in these cells.

Figure 2C:
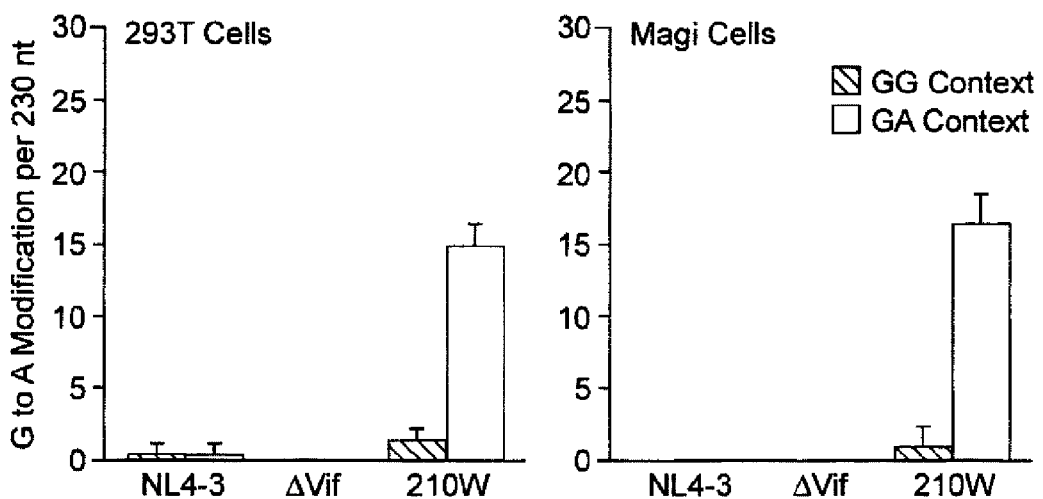
Figure 3:
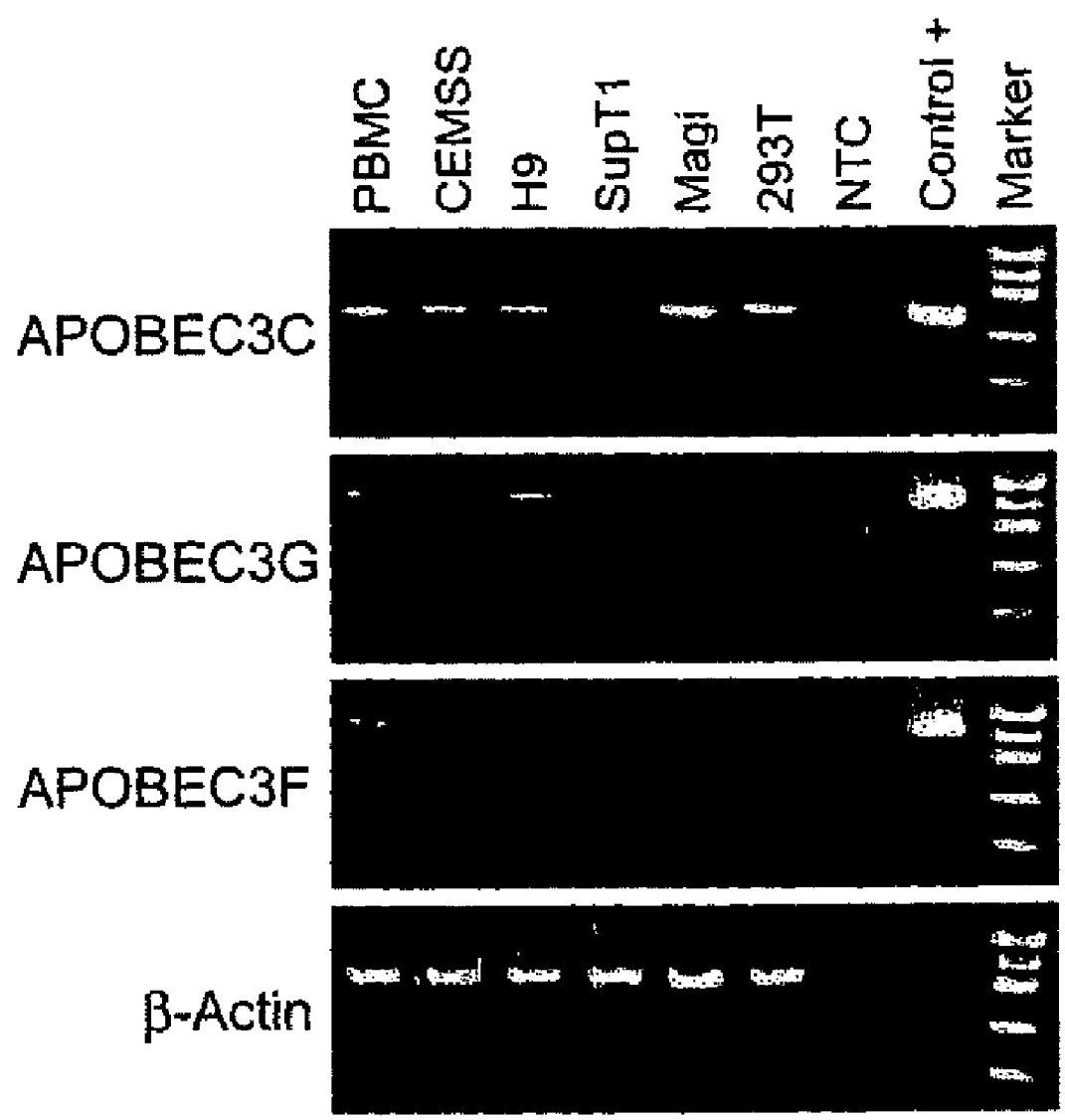
FIG. 3 depicts expression of APOBEC mRNAs in various cells.

FIGS. 2A-2C. G to A hypermutation is cell-type specific. DNA was isolated from cell cultures 5 days after infection with 210W, NL4-3 or NL4-1 Δvif. Viral DNA was amplified and the products were sequenced (FIG. 2A). The top line shows the 210W plasmid sequence (position 2255-2455). The G to A and other mutations are shown below the 210W sequence. Mutations were not observed after infection of SupT1 cells. The numbers of mutations relative to the plasmid were counted and displayed after infections if PBMC and CEMSS (FIG. 2B). Magi and 293T cells infected with pseudotyped viruses limited to a single cycle of replication display the same profile of G to A hypermutation observed in CEMSS (FIG. 2C).

Expression of APOBEC3C, 3G, 3F in PBMC and Cell Lines

To investigate whether the expression of h3C, h3F or h3G could explain cell-specific differences in mutational patterns, h3C, h3F and h3G ORFs were amplified by RT-PCR. PolyA+ RNA were isolated from PBMC and the H9, CEMSS, 293T, Magi and SupT1 cell lines. FIG. 3 shows that h3C mRNA is found in all cells except in the SupT1 cell line, where no G to A transitions are observed (FIG. 2A). This is consistent with the hypothesized role of h3C in 210W and NL4-3 mutation. The mRNAs for h3G and h3F were detected only in PBMC and the H9 cell line, suggesting that these deaminases may be responsible for the G to A transitions in a GG context observed in NL4-3 Δvif infections of these cells (FIG. 2B).

FIG. 3. Expression of APOBEC mRNA in different cells. Agarose gel showing the products of PCR reactions with primers specific for h3C, h3G and h3F. PCR templates were cDNAs for indicated cell types (see methods), or plasmids specific for h3C, h3G or h3F as positive controls. Water was the non-template control (NTC) and β-actin was used as an internal control.

Involvement of h3C in Hypermutation: as Shown by siRNA h3C Knockdown and h3C Overexpression To show that G to A hypermutation is eliminated when h3C expression is inhibited, siRNAs targeting h3C from position 167 to position 185 bases relative to the start codon, were used along with an RNA oligo conjugated to FITC to cotransfect Magi cells and 293T cells which express h3C but do not express h3G or h3F (FIG. 3). FITC positive cells were sorted after 48 h of transfection and maintained in culture for further analysis and infection.

h3C mRNA was not detectable by RT-PCR 48 h after transfection (FIG. 4). Scrambled RNA along with the FITC conjugated oligo RNA was used as a control and had no effect on h3C mRNA levels. In Magi cells transfected with siRNA, sorted for FITC positive and infected with 210W virus in a single round assay, G to A mutations were not detectable by sequencing (FIG. 4). In a parallel experiment performed with scrambled RNA, G to A mutations were detected in Magi also sorted for FITC and infected with 210W virus (FIG. 4). Inhibition of h3C expression by siRNA has a clear effect on 210W G to A transitions after infection of 293T cells as well.

RT-PCR analysis of APOBEC3B, APOBEC3C, APOBEC3F, and APOBEC3G mRNA from Magi cells transfected with either the anti-APOBEC3C siRNA or with the scrambled RNA control showed that the anti-APOBEC3C siRNA does not affect expression of APOBEC3B mRNA, APOBEC3F mRNA, or APOBEC3G mRNA. Thus, the anti-APOBEC3C siRNA selectively reduces APOBEC3C levels.

FIGS. 4A and 4B. Inhibition of h3C expression and G to A hypermutation by siRNA. Magi cells were transfected with 50 nM siRNAs directed against h3C, or with scrambled RNA, along with an oligo RNA conjugated with FITC. Cells were harvested 48 h later and sorted for FITC. PolyA+ RNA was isolated and RT-PCR was performed with primers specific for h3C. β-actin was used as internal control (FIG. 4A). These cells were then infected with the VSV-G pseudotyped HIV-1 210W, NL4.3 and Δvif strains, and cells were collected at 24 h following infection. Viral DNA was amplified as described in method and G to A modification was analyzed (FIG. 4B). Knockdown of h3C in 293T cells also abrogated the G to A hypermutation.

Figures 5A, 5B, 5C:
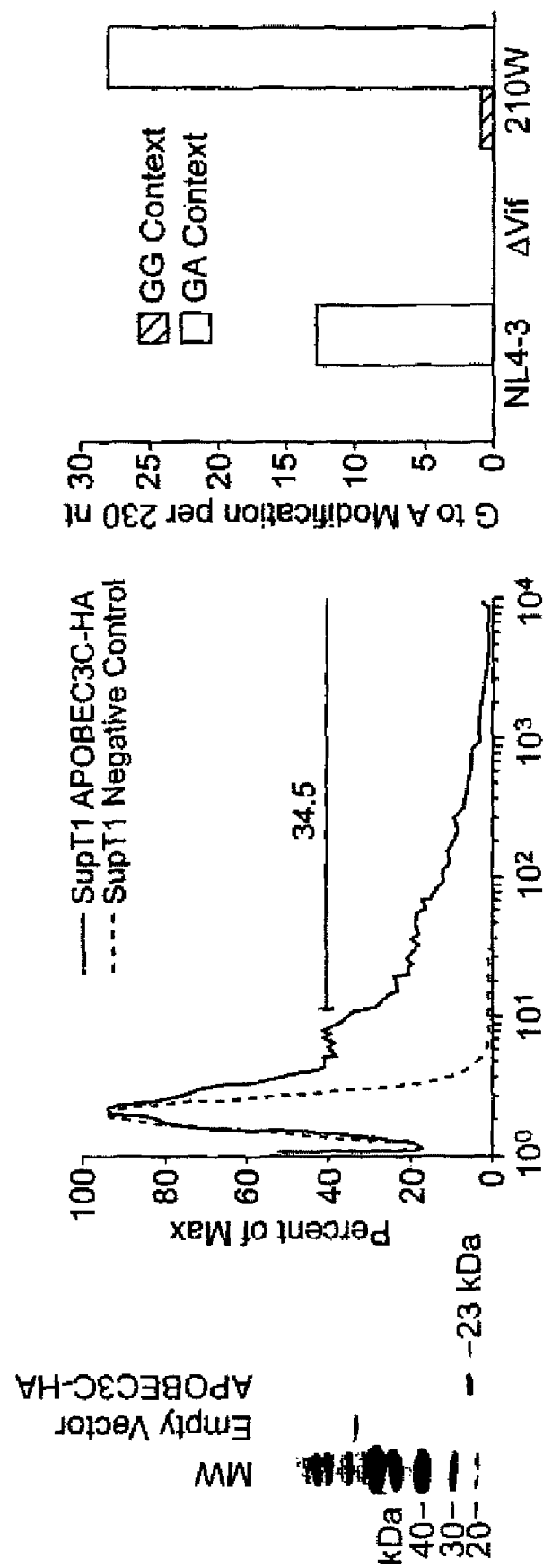
FIGS. 5A-C depict the effect of APOBEC3C expression on G to A mutations in proviral DNA in SupT1 cells.

Since APOBECs have some sequence homology, it is possible that in the siRNA knockdown affected APOBECs other than APOBEC3C. To ascertain that h3C was responsible for G to A mutations, SupT1 cells were transfected with h3C. SupT1 cells do not have G to A deaminase activity and do not express h3C mRNA (FIG. 3). The APOBEC3C was cloned into an expression plasmid that expresses the bicistronic h3C-IRES-GFP under R PGK promoter. A carboxyl-terminal influenza hemagglutinin (HA) epitope tag was attached by PCR. Western blot analysis of APOBEC3C protein expression in 293T transfected cells was performed using a polyclonal antibody specific for the tag. APOBEC3C protein displayed the predicted electrophoretic mobility of 23 kDa (FIG. 5A). APOBEC3C expression plasmid was then transfected into human SupT1 cells and the level of protein expression was assessed by quantifying GFP by FACS (FIG. 5B). After 48 h of transfection, the cells were infected with p24 normalized VSV-G pseudotyped NL4-3, Δvif and 210W viruses. After 24 h of infection, DNA was extracted, amplified and sequenced. The sequences showed that in SupT1 cells transfected with h3C, the level of G to A mutation detected in the 210W virus was high and almost completely restricted to the GA context while there was no hypermutation detected in SupT1 transfected with the empty vector (FIG. 5C). This result shows that cytoplasmic (transfected) h3C is responsible for G to A hypermutation in contrast to h3F and h3G which have to be incorporated into the virion in order to cause hypermutation.

FIGS. 5A-5C. Effect of APOBEC3C expression in SupT1. The h3C gene was cloned into the PPT-IRES-GFP lentiviral vector with HA tag. The protein was expressed in 293T cells and detected with a polyclonal HA antibody by Western blotting (FIG. 5A). This construct was used to transfect SupT1 cells. After 48 h, the efficiency of transfection was monitored in live gated cells by quantifying the level of GFP expression as measured by FACS analysis. Autofluorescence from non-transfected SupT1 cells was excluded from the measurement (FIG. 5B). The transfected SupT1 cells were infected with the VSV-G pseudotyped HIV-1 210W, NL4.3 or Δvif strains. Cells were collected at 24 h following infection. Viral DNA was amplified and the distribution of G to A mutations was assayed as described in FIG. 2 (FIG. 5C).

Example 2

Characterization of APOBEC3C-induced Mutations

Figure 7:
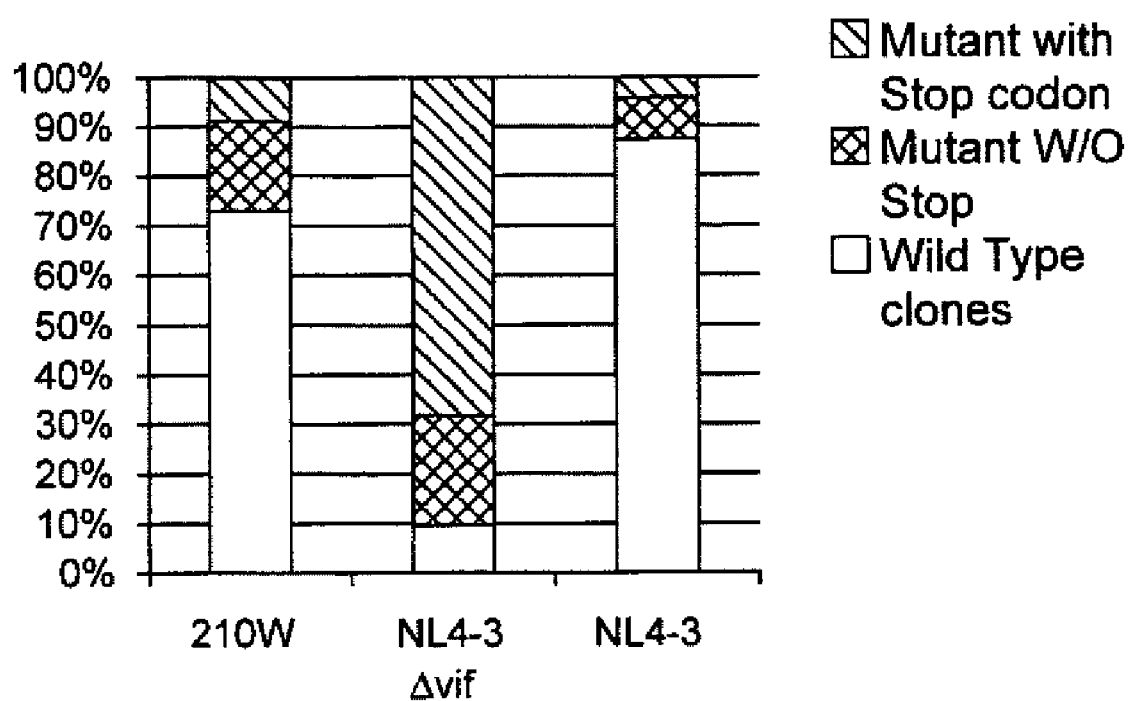
FIG. 7 depicts the mutation frequency introduced by APOBEC3C in HIV-1 210W, NL4-3Δvif, and NL4-3.

To understand why the G to A mutation introduced by APOBEC3C in HIV-1 210W does not lead to an antiviral effect, while this is a prominent feature of APOBEC3G and APOBEC3F action against vif deleted variants of HIV-1, PCR amplification of protease gene segments was carried out with primers that cannot distinguish between mutated and not mutated sequences. 210W and NL4-3 DNA from infected Peripheral Blood Mononuclear cells was amplified. The infection with NL4-3 Δvif virus was included as a positive control for lethal G-to-A mutation induced by APOBEC3G or APOBEC3F. The results are depicted schematically in FIG. 7. The clonal analysis virus population showed that out of 45 clones of 210W analyzed, 33 were wild type and 12 were mutated. Out of 47 clones of NL4-3 analyzed, 41 were wild type and 6 were mutated. Out of 41 clones of Δvif virus analyzed, 4 were wild type and 37 were mutated. The data demonstrate that the patient-derived isolate of HIV-1 is more susceptible to hypermutation in PBMCs, which express APOBEC3C. The rate of hypermutation is substantial, but less than the lethal amount of hypermutation observed in vif deleted variants that are susceptible to APOBEC3G and APOBEC3F. The decreased frequency of hypermutation in the patient-derived HIV-1 variant probably explains why the effect of APOBEC3C is not lethal.

Figure 8:
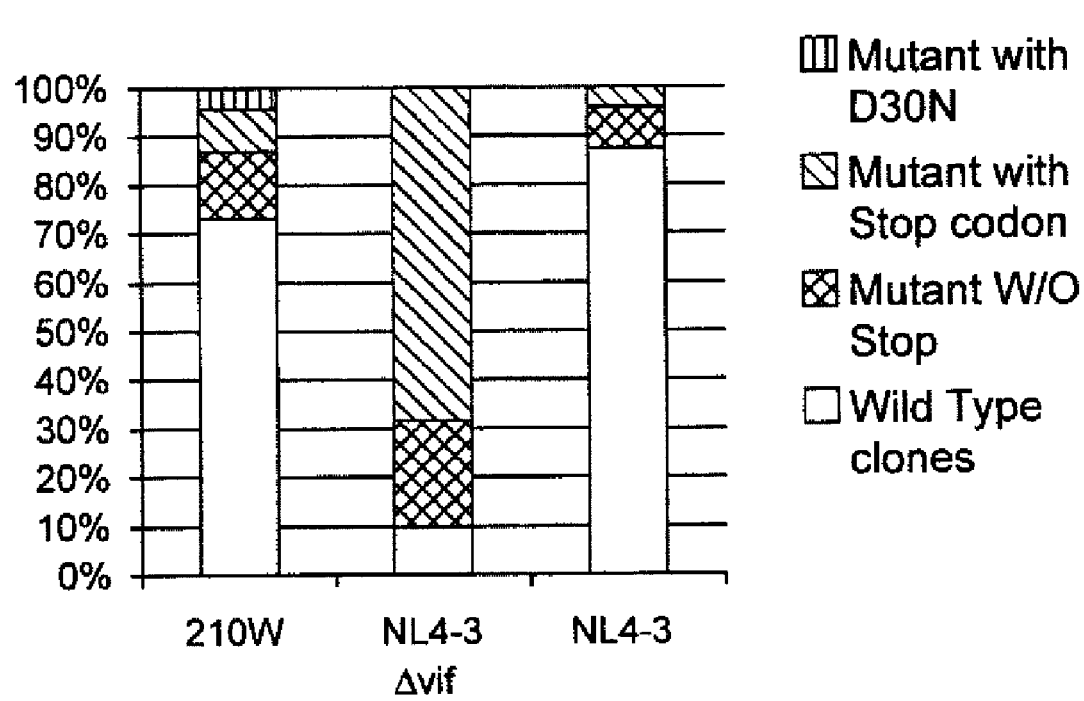
FIG. 8 depicts the results of an analysis of mutations in the protease encoded by 210W, NL4-3Δvif, and NL4-3.

To determine if the mutated proteases have acquired stop codons, the implications of mutations on the amino acid sequence were evaluated. The results are depicted schematically in FIG. 8. For 210W, out of 12 mutant clones, 4 had a stop codon and 8 were mutated without acquiring a stop codon, indicating that a mutant protease would be expressed. Of these mutant proteases, 2 had the D30N mutation which confers high level resistance to the protease inhibitor nelfinavir. These data demonstrate that APOBEC3C action yields viable and drug resistant variants of HIV-1 in primary human tissues. As controls, for NL4-3, 2 clones have stop codon and 4 are mutated without stop codon. For Δvif virus, 28 clones have stop codon and 9 were highly mutated but without having stop codon.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An in vitro method of identifying an agent that reduces the level of active APOBEC3C in a cell, the method comprising:
   a) contacting a cell that produces an APOBEC3C protein with a test agent, wherein the cell comprises a replication-competent Vif+ human immunodeficiency virus (HIV) proviral construct, said virus being susceptible to the effects of APOBEC3C; and
   b) determining i) the number of C→U mutations induced in the minus strand of virus expressed from the proviral construct; ii) the number of G→A mutations in a reverse transcript of the expressed virus; or iii) the number of C→T mutations in the provirus.

2. The method of claim 1, wherein the APOBEC3C protein is a fusion protein comprising APOBEC3C and a fusion partner that provides a detectable signal.

3. The method of claim 2, wherein the fusion partner is selected from a fluorescent protein, an enzyme, and an immunological tag.

4. The method of claim 1, wherein said determining step comprises determining the number of C→U mutations induced in the minus strand of the HIV construct.

5. The method of claim 1, wherein the APOBEC3C protein is encoded by an expression vector.

6. The method of claim 1, wherein the cell is a mammalian cell.

7. The method of claim 1, wherein said determining step comprises determining the number of G→A mutations in a reverse transcript of the expressed virus.

8. The method of claim 1, wherein said determining step comprises determining the number of C→T mutations in the provirus.

* * * * *

SEQUENCE LISTING

<160> NUMBER OF SEQ ID NOS: 19

<210> SEQ ID NO 1
<211> LENGTH: 10
<212> TYPE: PRT
<213> ORGANISM: Artificial Sequence
<220> FEATURE:
<223> OTHER INFORMATION: epitope tag

<400> SEQUENCE: 1

```
Cys Tyr Pro Tyr Asp Val Pro Asp Tyr Ala
 1               5                  10

<210> SEQ ID NO 2
<211> LENGTH: 8
<212> TYPE: PRT
<213> ORGANISM: Artificial Sequence
<220> FEATURE:
<223> OTHER INFORMATION: epitope tag

<400> SEQUENCE: 2

Asp Tyr Lys Asp Asp Asp Asp Lys
 1               5

<210> SEQ ID NO 3
<211> LENGTH: 11
<212> TYPE: PRT
<213> ORGANISM: Artificial Sequence
<220> FEATURE:
<223> OTHER INFORMATION: epitope tag

<400> SEQUENCE: 3

Cys Glu Gln Lys Leu Ile Ser Glu Glu Asp Leu
 1               5                  10

<210> SEQ ID NO 4
<211> LENGTH: 190
<212> TYPE: PRT
<213> ORGANISM: H. sapiens

<400> SEQUENCE: 4

Met Asn Pro Gln Ile Arg Asn Pro Met Lys Ala Met Tyr Pro Gly Thr
 1               5                  10                  15

Phe Tyr Phe Gln Phe Lys Asn Leu Trp Glu Ala Asn Asp Arg Asn Glu
                 20                  25                  30

Thr Trp Leu Cys Phe Thr Val Glu Gly Ile Lys Arg Arg Ser Val Val
             35                  40                  45

Ser Trp Lys Thr Gly Val Phe Arg Asn Gln Val Asp Ser Glu Thr His
 50                  55                  60

Cys His Ala Glu Arg Cys Phe Leu Ser Trp Phe Cys Asp Asp Ile Leu
 65                  70                  75                  80

Ser Pro Asn Thr Lys Tyr Gln Val Thr Trp Tyr Thr Ser Trp Ser Pro
                 85                  90                  95

Cys Pro Asp Cys Ala Gly Glu Val Ala Glu Phe Leu Ala Arg His Ser
            100                 105                 110

Asn Val Asn Leu Thr Ile Phe Thr Ala Arg Leu Tyr Tyr Phe Gln Tyr
                115                 120                 125

Pro Cys Tyr Gln Glu Gly Leu Arg Ser Leu Ser Gln Glu Gly Val Ala
            130                 135                 140

Val Glu Ile Met Asp Tyr Glu Asp Phe Lys Tyr Cys Trp Glu Asn Phe
145                 150                 155                 160

Val Tyr Asn Asp Asn Glu Pro Phe Lys Pro Trp Lys Gly Leu Lys Thr
                165                 170                 175

Asn Phe Arg Leu Leu Lys Arg Arg Leu Arg Glu Ser Leu Gln
            180                 185                 190

<210> SEQ ID NO 5
<211> LENGTH: 200
<212> TYPE: DNA
<213> ORGANISM: HIV-1
```

<400> SEQUENCE: 5
tcagatcact ctttggcaac gacccctcgt cacaataaag atagggggc aactaaagga      60 agctctatta gacacaggag cagatgatac agtattagaa gaaatgaatt tgccaggaag     120
atggaaacca aaaatgatag ggggaattgg aggttttatc aaagtaagac agtatgatca     180
gataccaata gaaatctgcg                                                 200

<210> SEQ ID NO 6
<211> LENGTH: 200
<212> TYPE: DNA
<213> ORGANISM: Artificial Sequence
<220> FEATURE:
<223> OTHER INFORMATION: HIV-1 mutant

<400> SEQUENCE: 6
tcaaatcact ctttggcaac aacccctcgt cacaataaag atagggggc aactagaaaa      60 agctctatta aacacaaaag caaataatac agtattaaaa aaaataaatt tgccaaaaaa     120
ataaaaacca aaaataataa aaaaaattaa aaattttatc aaagtaaaac agtataatca     180
aataccaata aaaatctgca                                                 200

<210> SEQ ID NO 7
<211> LENGTH: 200
<212> TYPE: DNA
<213> ORGANISM: Artificial Sequence
<220> FEATURE:
<223> OTHER INFORMATION: HIV-1 mutant

<400> SEQUENCE: 7
tcaaatcact ctttggcaac aacccctcgt cacaataaaa ataaggggc aactaaaaaa      60 agctctatta aacacaggag caaataatac agtattaaaa aaaataaatt tgccaaaaaa     120
ataaaaacca aaaataataa gggaaattaa aggttttatc aaagtaaaac agtataatca     180
aataccaata aaaatctgcg                                                 200

<210> SEQ ID NO 8
<211> LENGTH: 200
<212> TYPE: DNA
<213> ORGANISM: Artificial Sequence
<220> FEATURE:
<223> OTHER INFORMATION: HIV-1 mutant

<400> SEQUENCE: 8
tcaaatcact ctttggcaac gacccctcgt cacaataaag atagggggc aactaaagaa      60 agctctatta aacacaggag cagataatac agtattagaa aaaataaatt tgccaggaaa     120
atgaaaacca aaaatgatag ggggaattga aggttttatc aaagtaagac agtataatca     180
gataccaata gaaatctgcg                                                 200

<210> SEQ ID NO 9
<211> LENGTH: 200
<212> TYPE: DNA
<213> ORGANISM: Artificial Sequence
<220> FEATURE:
<223> OTHER INFORMATION: HIV-1 mutant

<400> SEQUENCE: 9
tcaaatcact ctttggcaac gacccctcgt cacaataaag atagggggc aactaaagaa      60 agctctatta aacacaggag caaataatac agtattaaaa aaaataaatt tgccaggaaa     120
ataaaaacca aaaataatag ggggaattaa aggttttatc aaagtaagac agtataatca     180

```
aataccaata aaaatctgcg                                                  200

<210> SEQ ID NO 10
<211> LENGTH: 200
<212> TYPE: DNA
<213> ORGANISM: Artificial Sequence
<220> FEATURE:
<223> OTHER INFORMATION: HIV-1 mutant

<400> SEQUENCE: 10
tcaaatcact ctttggcaac gaccgctcgt cacaataaag ataggggggc aactaaaaga      60
agctctatta gacacagaag cagataatac agtattaaaa aaaataaatt tgccagaaaa     120
atgaaaacca aaataatag gaaaaattaa agtttttatc aaagtaaaac agtataatca     180
aataccaata aaaatctgcg                                                  200

<210> SEQ ID NO 11
<211> LENGTH: 200
<212> TYPE: DNA
<213> ORGANISM: Artificial Sequence
<220> FEATURE:
<223> OTHER INFORMATION: HIV-1 mutant

<400> SEQUENCE: 11
tcaaatcact ctttggcaac aaccgctcgt cacaataaag ataggggggc aactaaaaga      60
agctctatta gacacagaag cagataatac agtattaaaa aaaataaatt tgccagaaaa     120
atgaaaacca aaataatag ggggaattaa agtttttatc aaagtaaaac agtataatca     180
aataccaata gaaatctgcg                                                  200

<210> SEQ ID NO 12
<211> LENGTH: 22
<212> TYPE: DNA
<213> ORGANISM: Artificial Sequence
<220> FEATURE:
<223> OTHER INFORMATION: primer

<400> SEQUENCE: 12
atgaatccac agatcagaaa cc                                                22

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
tcactggaga ctctcccgta                                                   20

<210> SEQ ID NO 14
<211> LENGTH: 21
<212> TYPE: DNA
<213> ORGANISM: Artificial Sequence
<220> FEATURE:
<223> OTHER INFORMATION: primer

<400> SEQUENCE: 14
atgaagcctc acttcagaaa c                                                 21

<210> SEQ ID NO 15
<211> LENGTH: 19
<212> TYPE: DNA
<213> ORGANISM: Artificial Sequence
<220> FEATURE:
```

-continued

```
<223> OTHER INFORMATION: primer

<400> SEQUENCE: 15
tcactcgaga atctcctgc                                                19

<210> SEQ ID NO 16
<211> LENGTH: 25
<212> TYPE: DNA
<213> ORGANISM: Artificial Sequence
<220> FEATURE:
<223> OTHER INFORMATION: primer

<400> SEQUENCE: 16
atgaagcctc acttcagaaa cacag                                         25

<210> SEQ ID NO 17
<211> LENGTH: 26
<212> TYPE: DNA
<213> ORGANISM: Artificial Sequence
<220> FEATURE:
<223> OTHER INFORMATION: primer

<400> SEQUENCE: 17
tcagttttcc tgattctgga gaatgg                                        26

<210> SEQ ID NO 18
<211> LENGTH: 40
<212> TYPE: DNA
<213> ORGANISM: Artificial Sequence
<220> FEATURE:
<223> OTHER INFORMATION: primer

<400> SEQUENCE: 18
cgcggatccg ccgccaccat gaatccacag atcagaaacc                         40

<210> SEQ ID NO 19
<211> LENGTH: 65
<212> TYPE: DNA
<213> ORGANISM: Artificial Sequence
<220> FEATURE:
<223> OTHER INFORMATION: primer

<400> SEQUENCE: 19
tgctctagac tagaggctag cgtaatccgg aacatcgtat gggtactgga gactctcccg   60
tagcc                                                               65
```